United States Patent
Weinberg et al.

[11] Patent Number: 5,959,297
[45] Date of Patent: Sep. 28, 1999

[54] MASS SPECTROMETERS AND METHODS FOR RAPID SCREENING OF LIBRARIES OF DIFFERENT MATERIALS

[75] Inventors: W. Henry Weinberg, Woodside; Eric W. McFarland, San Jose; Peijun Cong, Cupertino; Shenheng Guan, San Jose, all of Calif.

[73] Assignee: Symyx Technologies, Santa Clara, Calif.

[21] Appl. No.: 08/946,730

[22] Filed: Oct. 8, 1997

Related U.S. Application Data

[63] Continuation-in-part of application No. 08/898,715, Jul. 22, 1997.
[60] Provisional application No. 60/050,949, Jun. 13, 1997, provisional application No. 60/028,106, Oct. 9, 1996, provisional application No. 60/029,255, Oct. 25, 1996, provisional application No. 60/035,366, Jan. 10, 1997, provisional application No. 60/048,987, Jun. 9, 1997, provisional application No. 60/028,105, Oct. 9, 1996, and provisional application No. 60/035,202, Jan. 10, 1997.

[51] Int. Cl.⁶ .................................................. H01J 49/00
[52] U.S. Cl. ............................................................. 250/288
[58] Field of Search ............................... 250/288, 288 A, 250/423 R, 425, 281, 282

[56] References Cited

U.S. PATENT DOCUMENTS

| | | | |
|---|---|---|---|
| 3,758,777 | 9/1973 | Brunnee et al. | 250/288 |
| 3,944,826 | 3/1976 | Gray | 250/288 |
| 5,077,470 | 12/1991 | Cody et al. | 250/282 |
| 5,146,088 | 9/1992 | Kingham et al. | 250/288 |
| 5,210,412 | 5/1993 | Levis et al. | 250/288 |
| 5,244,814 | 9/1993 | Barbour et al. | 250/288 |
| 5,528,032 | 6/1996 | Uchiyama | 250/288 |
| 5,770,860 | 6/1998 | Franzen | 250/288 |

FOREIGN PATENT DOCUMENTS

| | | |
|---|---|---|
| 0 260 469 A2 | 8/1987 | European Pat. Off. . |
| 0 408 487 A2 | 6/1990 | European Pat. Off. . |
| WO 95/25737 | 9/1995 | WIPO . |
| WO 96/11878 | 4/1996 | WIPO . |
| WO 96/22530 | 7/1996 | WIPO . |

OTHER PUBLICATIONS

Huang, Yulin, et al., "Collision–Induced Dissociation of Mass Spectrometric Analysis of Biopolymers: High–Resolution Fourier Transform Ion Cyclotron Resonance MS," *Analytical Chemistry*, vol. 66, No. 24, pp. 4385–4389 (1994).

Kelly, Michele, et al., "Characterization of SH2–Ligand Interactions via Library Affinity Selection with Mass Spectrometric Detection," *Biochemistry*, vol.35, No. 36, pp. 11747–11755 (1996).

*Primary Examiner*—Kiet T. Nguyen
*Attorney, Agent, or Firm*—Rader, Fishman & Grauer PLLC

[57] ABSTRACT

Methods and apparatus for screening diverse arrays of materials are provided. Techniques are provided for rapidly characterizing compounds in combinatorial arrays of materials for discovering and/or optimizing new materials with specific desired properties. A scanning mass spectrometer is used which includes an ionization chamber and a collector that outputs an electrical signal responsive to the quantity of gas ions contacting the collector surface. A conduit system selectively withdraws samples from the array of materials, passing the samples into the ionization chamber. In a specific embodiment, reactants are passed through the conduit system to the selected regions of interest on the substrate.

35 Claims, 9 Drawing Sheets

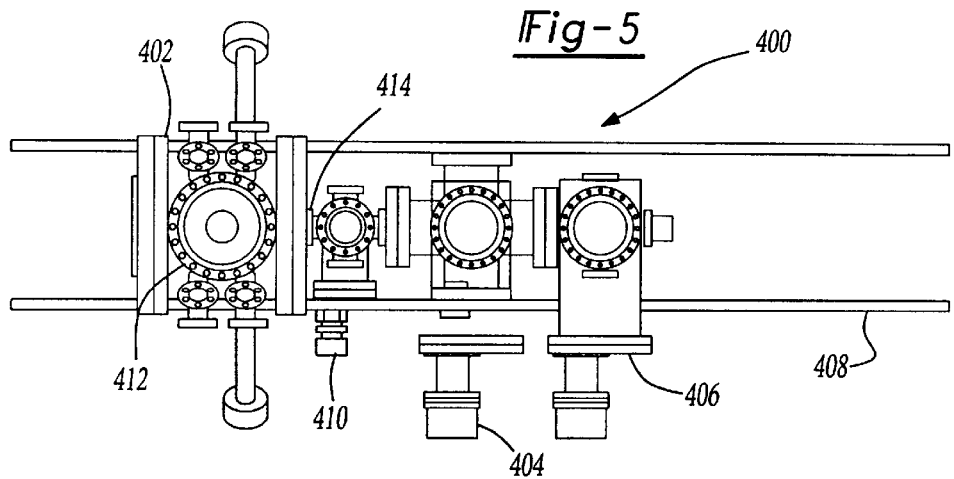
*Fig-5*
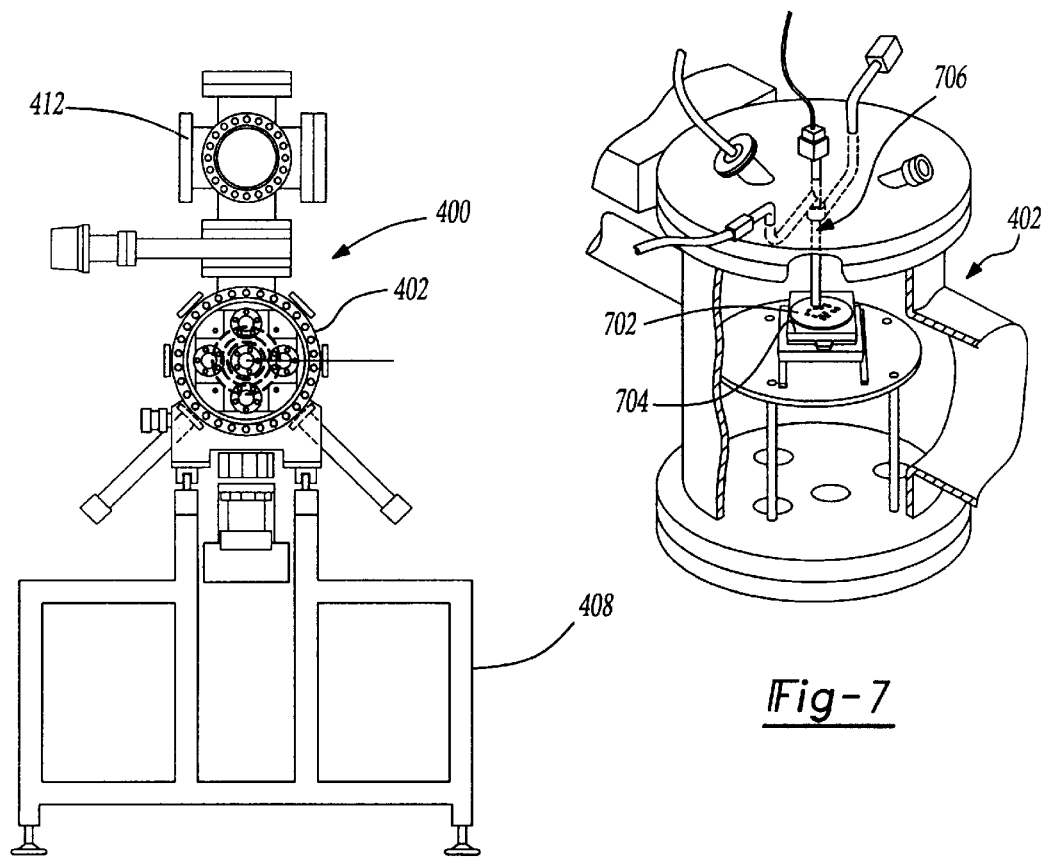
*Fig-6*
*Fig-7*

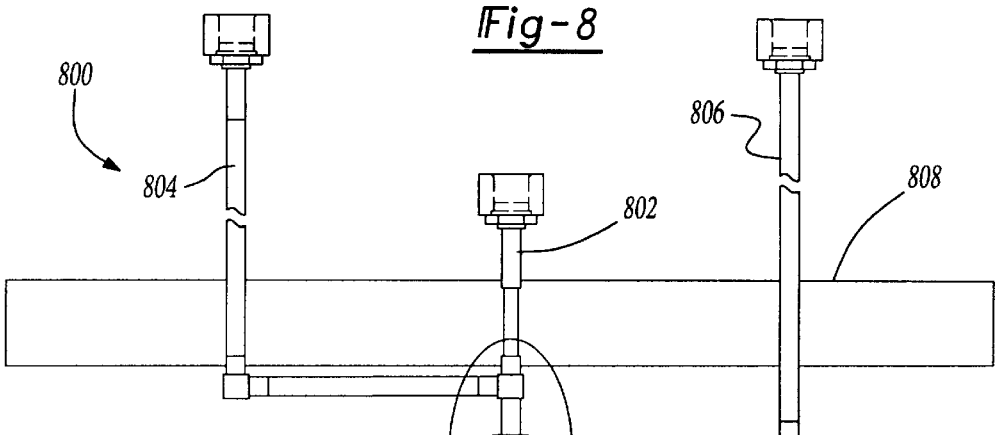
Fig-8
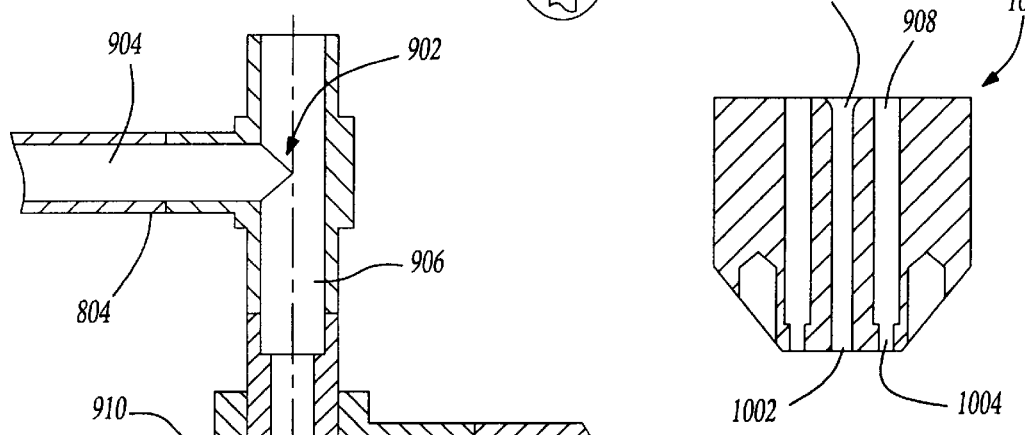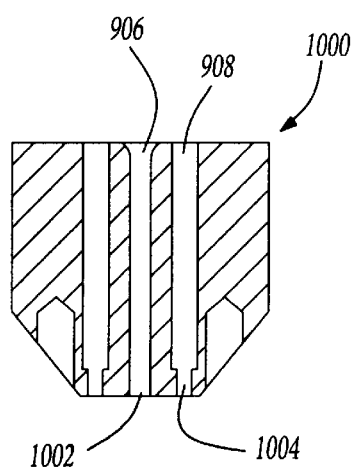
Fig-9
Fig-10
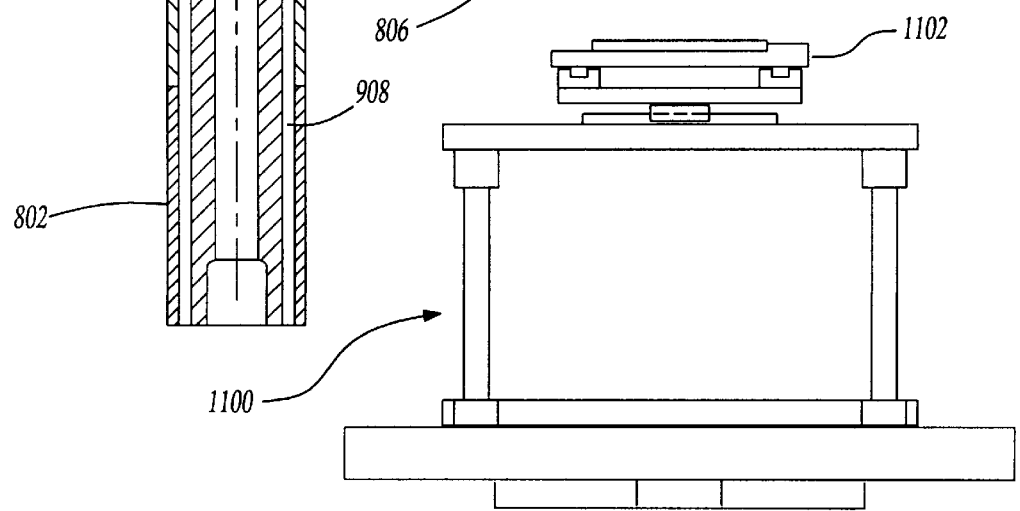
Fig-11

$\dfrac{\Delta h}{\Delta z} = 22.86$

MASS SPECTROMETERS AND METHODS FOR RAPID SCREENING OF LIBRARIES OF DIFFERENT MATERIALS

CROSS REFERENCE TO RELATED APPLICATIONS

This application is a continuation-in-part of commonly assigned U.S. patent application Ser. No. 08/898,715, filed Jul. 22, 1997, and a continuation-in-part of commonly assigned, co-pending U.S. Provisional Applications Serial Nos. 60/050,949, filed Jun. 13, 1997; 60/028,106, filed Oct. 9, 1996; 60/029,255, filed Oct. 25, 1996; 60/035,366, filed Jan. 10, 1997; 60/048,987, filed Jun. 9, 1997; 60/028,105, filed Oct. 9, 1996; and 60/035,202, filed Jan. 10, 1997; the complete disclosures of which are incorporated herein by reference for all purposes.

This application is also related to commonly assigned, co-pending U.S. patent applications Ser. No. 08/327,513, filed Oct. 18, 1994, Ser. No. 08/438,043, filed May 8, 1995, and Ser. No. 08/841,423, filed Apr. 22, 1997; commonly assigned U.S. Provisional Application Serial No. 60/016, 102, filed Jul. 23, 1996; and PCT Application No. WO 95/13278, filed Oct. 18, 1995; the complete disclosures of which are incorporated herein by reference for all purposes.

FIELD OF THE INVENTION

The present invention generally relates to methods and apparatus for rapidly screening an array of diverse materials that have been created at known locations on a single substrate surface. More specifically, the invention is directed to scanning mass spectrometers and their application to screening libraries of different materials.

BACKGROUND OF THE INVENTION

The discovery of new materials with novel chemical and physical properties often leads to the development of new and useful technologies. Currently, there is a tremendous amount of activity in the discovery and optimization of materials, such as superconductors, zeolites, magnetic materials, phosphors, catalysts, thermoelectric materials, high and low dielectric materials and the like. Unfortunately, even though the chemistry of extended solids has been extensively explored, few general principles have emerged that allow one to predict with certainty the composition, structure and reaction pathways for the synthesis of such solid state compounds.

The preparation of new materials with novel chemical and physical properties is at best happenstance with our current level of understanding. Consequently, the discovery of new materials depends largely on the ability to synthesize and analyze new compounds. Given approximately 100 elements in the periodic table that can be used to make compositions consisting of two or more elements, an incredibly large number of possible new compounds remains largely unexplored. As such, there exists a need in the art for a more efficient, economical and systematic approach for the synthesis of novel materials and for the screening of such materials for useful properties.

One of the processes whereby nature produces molecules having novel functions involves the generation of large collections (libraries) of molecules and the systematic screening of those collections for molecules having a desired property. An example of such a process is the humoral immune system which in a matter of weeks sorts through some $10^{12}$ antibody molecules to find one which specifically binds a foreign pathogen (Nisonoff et al., *The Antibody Molecule* (Academic Press, New York, 1975)). This notion of generating and screening large libraries of molecules has recently been applied to the drug discovery process.

Applying this logic, methods have been developed for the synthesis and screening of large libraries (up to $10^{14}$ molecules) of peptides, oligonucleotides and other small molecules. Geysen et al., for example, have developed a method wherein peptide syntheses are carried out in parallel on several rods or pins (*J. Immun. Meth.* 102:259–274 (1987), incorporated herein by reference for all purposes). Generally, the Geysen et al. method involves functionalizing the termini of polymeric rods and sequentially immersing the termini in solutions of individual amino acids. In addition to the Geysen et al. method, techniques have recently been introduced for synthesizing large arrays of different peptides and other polymers on solid surfaces. Pirrung et al. have developed a technique for generating arrays of peptides and other molecules using, for example, light-directed, spatially-addressable synthesis techniques (U.S. Pat. No. 5,143,854 and PCT Publication No. WO 90/15070, incorporated herein by reference for all purposes). In addition, Fodor et al. have developed a method of gathering fluorescence intensity data, various photosensitive protecting groups, masking techniques, and automated techniques for performing light-directed, spatially-addressable synthesis techniques (Fodor et al., PCT Publication No. WO 92/10092, the teachings of which are incorporated herein by reference for all purposes).

Using these various methods, arrays containing thousands or millions of different elements can be formed (U.S. patent application No. 08/805,727, filed Dec. 6, 1991, the complete disclosure of which is incorporated herein by reference for all purposes). As a result of their relationship to semiconductor fabrication techniques, these methods have come to be referred to as "Very Large Scale Immobilized Polymer Synthesis," or "VLSIPS™" technology. Such techniques have met with substantial success in screening various ligands such as peptides and oligonucleotides to determine their relative binding affinity to a receptor such as an antibody.

The solid phase synthesis techniques currently being used to prepare such libraries involve the sequential coupling of building blocks to form the compounds of interest. For example, in the Pirrung et al. method polypeptide arrays are synthesized on a substrate by attaching photoremovable groups to the surface of the substrate, exposing selected regions of the substrate to light to activate those regions, attaching an amino acid monomer with a photoremovable group to the activated region, and repeating the steps of activation and attachment until polypeptides of the desired length and sequence are synthesized. These solid phase synthesis techniques cannot readily be used to prepare many inorganic and organic compounds.

In PCT WO 96/11878, the complete disclosure of which is incorporated herein by reference, methods and apparatus are disclosed for preparing a substrate with an array of diverse materials deposited in predefined regions. Some of the methods of deposition disclosed in PCT WO 96/11878 include sputtering, ablation, evaporation, and liquid dispensing systems. Using the disclosed methodology, many classes of materials can be generated combinatorially including inorganics, intermetallics, metal alloys, and ceramics.

In general, combinatorial chemistry refers to the approach of creating vast numbers of compounds by reacting a set of starting chemicals in all possible combinations. Since its introduction into the pharmaceutical industry in the late 80's, it has dramatically sped up the drug discovery process and is now becoming a standard practice in the industry (*Chem. Eng. News* Feb. 12, 1996). More recently, combinatorial techniques have been successfully applied to the synthesis of inorganic materials (G. Briceno et al., *SCIENCE* 270, 273–275, 1995 and X. D. Xiang et al., *SCIENCE* 268, 1738–1740, 1995). By use of various surface deposition techniques, masking strategies, and processing conditions, it is now possible to generate hundreds to thousands of materials of distinct compositions per square inch. These materials include high $T_c$ superconductors, magnetoresistors, and phosphors. Discovery of heterogeneous catalysts will no doubt be accelerated by the introduction of such combinatorial approaches.

A major difficulty with these processes is the lack of fast and reliable testing methods for rapid screening and optimization of the materials. Recently, a parallel screening method based on reaction heat formation has been reported (F. C. Moates et al., *Ind. Eng. Chem. Res.* 35, 4801–4803, 1996). For oxidation of hydrogen over a metallic surface, it is possible to obtain IR radiation images of an array of catalysts. The hot spots in the image correspond to active catalysts and can be resolved by an infrared camera.

Screening large arrays of materials in combinatorial libraries creates a number of challenges for existing analytical techniques. For example, traditionally, a heterogeneous catalyst is characterized by the use of a micro-reactor that contains a few grams of porous-supported catalysts. Unfortunately, the traditional method cannot be used to screen a catalyst library generated with combinatorial methods. First, a heterogeneous catalyst library synthesized by a combinatorial chemistry method may contain from a few hundred to many thousands of catalysts. It is impractical to synthesize a few grams of each catalyst in a combinatorial format. Second, the response time of micro-reactors is typically on the order of a few minutes. The time it takes to reach equilibrium conditions is even longer. It is difficult to achieve high-throughput screening with such long response times.

Another challenge with screening catalyst arrays is the low concentration of components that may be present in the reactions. For example, oxidation of ethylene to ethylene oxide can be carried out over a silver-based catalyst (S. Rebsdat et al., U.S. Pat. Nos. 4,471,071 and 4,808,738). For a surface-supported catalyst with an area of 1 mm by 1 mm and the same activity as the industrial catalyst, only about 10 parts per billion (ppb) of ethylene are converted into the desired ethylene oxide when the contact time is one second.

Detection of such low component levels in the presence of several atmospheres of reaction mixture is a challenge to analytical methods. Many analytical techniques, including optical methods such as four-wave mixing spectroscopy and cavity ring-down absorption spectroscopy as well as conventional methods such as GC/MS, are excluded because of poor sensitivities, non-universal detectability, and/or slow response.

A viable option is direct mass spectrometric detection, which is a sensitive and flexible molecular detection technique that can be operated at high speed. Commercially available mass spectrometers cannot be employed directly for catalyst screening. Magnetic-sector based mass spectrometers offer high dynamic range, but suffer from low sensitivity. Quadrupole MS based residual gas analyzers (RGAs) provide good sensitivity and modest mass resolution. The dynamic range of RGAs is on the order of $10^6$ which, for many important catalytic reactions with low conversion, is about two orders of magnitude lower than what is needed. Therefore an apparatus and methodology for screening a substrate having an array of materials that differ slightly in chemical composition, concentration, stoichiometry, and/or thickness is desirable.

SUMMARY OF THE INVENTION

The present invention provides methods and apparatus for interrogating an array of diverse materials located at predefined regions on a substrate using a mass spectrometer specifically engineered for library interrogation. Typically, each of the individual materials will be screened or interrogated for the same material characteristic. Once screened, the individual materials may be ranked or otherwise compared relative to each other with respect to the material characteristic under investigation. Materials, which can be compared using the methods and apparatus of the present invention, include, for example, covalent network solids, ionic solids, molecular solids, and gas or liquid phase molecules produced by reactions occurring on solid or liquid catalyst systems.

More specifically, the present invention is directed to systems and methods for screening libraries of at least 9 different materials contained on a single substrate. The screening process can be used to determine the relative concentrations of reactants and products in close proximity to a compound as well as to determine the relative concentrations or identities of molecules within a condensed phase. In particular, a scanning mass spectrometer is used in accordance with the present invention.

In one aspect of the present invention, a scanning mass spectrometer is used to characterize materials located at predefined locations within an array. The spectrometer system includes a housing with an ionization chamber and a collector. The collector has a surface that outputs an electrical signal in response to the quantity of gas ions contacting the collector surface. The system also includes a conduit system for drawing or sampling materials in the vicinity of predefined locations on the substrate array into the ionization chamber.

In one embodiment, the system utilizes a conduit as a sampling probe. The probe includes a capillary having an opening positioned over the predefined location of interest on the array. Typically the probe opening is on the order of about 0.02 to 0.05 mm although other sizes may be required depending upon the density of material regions on the array. The proximal end of the probe conduit is coupled to the ionization chamber. A translation stage, coupled to the sample holder, provides a means of positioning a specific region under the probe opening. If desired, the translation stage can scan the entire array under the probe, thus sequentially screening each of the predefined locations on the array.

In a specific configuration, the mass spectrometer includes a reaction chamber housing the substrate holder and the translation stage. In this configuration the conduit system includes a single sampling probe having a distal capillary positioned over the substrate holder for scanning across the substrate within the reaction chamber. Gas reactants are introduced into the reaction chamber in order to generate reactions with the materials contained on the substrate. The gas reactants may be introduced directly into the chamber so that reactions occur simultaneously across the entire substrate, or they may be introduced through the sampling probe so that the reactions occur sequentially as the probe scans across the substrate. In either embodiment, the system preferably scans and measures an array at rates of approximately 1 library element every 10 seconds. In other configurations, the scan/measure rate is substantially slower or faster, for example, slower than 1 library element every 100 seconds or faster than 10, 100, or 1000 library elements per second.

In another embodiment, an array of spaced conduits is positioned over the array of materials on the substrate for drawing gases from these locations into the ionization chamber. Preferably, each conduit includes an inlet passage for delivering reactant gases to the predefined locations and an outlet passage for drawing the gas products into the mass spectrometer. In addition, each conduit includes a valve so that the reactions can be sequentially created to allow sequential screening of the resulting gas products. Alternatively, the reactions may be created simultaneously, with sequential screening accomplished by different flow rates through the outlet passages.

In a specific embodiment, the mass spectrometer further comprises a mass filter or ion guide located between the ionization chamber and the collector or mass detector. The ion guide is used to increase the dynamic range of the spectrometer by selectively blocking or rejecting charged particles of an undesirable mass-to-charge ratio. Preferably the ion guide provides two orders of magnitude of purification, only passing a concentrated beam of the ions of interest to the mass detector. In this manner, the mass spectrometer is preferably capable of sampling 1 ml per second at one atmosphere with a detectable dynamic range of $10^8$. This high dynamic range and high speed allows the spectrometer to screen large arrays of materials, on the order of $10^6$ materials, in which there is a low level of reaction components, for example, a catalytic material having a low conversion rate.

In one embodiment, the system includes an energy source for selectively applying energy to a predefined region in order to monitor for activity or a desired product. In a specific embodiment, the energy source comprises a heat transfer system positioned below the substrate holder for heating selected predefined locations on the substrate. Heating of the library can be performed simultaneously or sequentially, using an infrared source (i.e., lamp, laser, etc.) or resistive heaters.

In an alternative embodiment, a laser is incorporated into the system. The laser beam is used to deliver sufficient energy to the condensed phase of a material at a predefined location on the substrate to vaporize molecules from the material allowing them to be detected in the mass spectrometer. Once the molecules are in the vapor phase, they are moved through the conduit into the mass spectrometer wherein their masses are identified.

A further understanding of the nature and advantages of the inventions herein may be realized by reference to the remaining portions of the specification and the attached drawings.

BRIEF DESCRIPTION OF THE DRAWINGS

FIG. 5 is a top view of a specific embodiment of a scanning mass spectrometer according to the present invention;

FIG. 6 is a front view of a specific embodiment of a scanning mass spectrometer according to the present invention;

FIG. 7 is a partial sectional view of a reaction chamber within the scanning mass spectrometer of FIGS. 4–6;

FIG. 8 is a side view of a conduit system;

FIG. 9 is an expanded cross-sectional view of a sampling probe of the conduit system shown in FIG. 8;

FIG. 10 is an enlarged view of the distal capillary of the sampling probe shown in FIG. 9;

FIG. 11 is a side view of a substrate holder and a translation stage for moving a substrate relative to the probe shown in FIGS. 9 and 10;

DETAILED DESCRIPTION OF THE INVENTION AND PREFERRED EMBODIMENTS

Glossary

Figure 1:
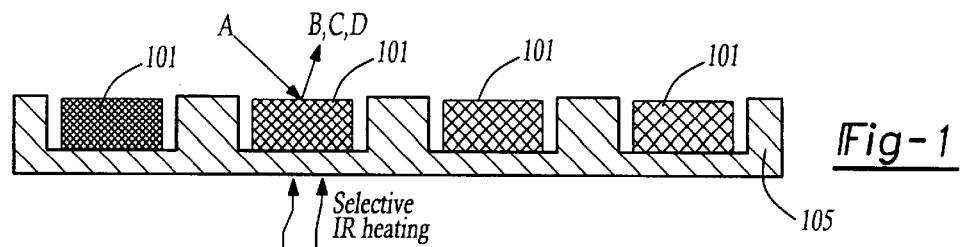
FIG. 1 illustrates a configuration for selective heating of materials on a substrate according present invention.

The following terms are intended to have the following general meanings as used herein.

Substrate

A substrate is a material having a rigid or semi-rigid surface. In many embodiments at least one surface of the substrate will be substantially flat. In some embodiments the substrate will contain physical separations between synthesis regions for different materials. Suitable physical separations include, for example, dimples, wells, raised regions, and etched trenches. According to other embodiments, small beads or pellets may be provided on the surface, either alone or within substrate surface dimples. The surface area of the substrate is designed to meet the requirements of a particular application. Typically, the surface area of the substrate is in the range of 1 $cm^2$ to 400 $cm^2$. However, other sizes may be used with the present invention, for example surface areas as small as 0.001 $cm^2$ or as large as 10 $m^2$ are possible.

Predefined Region

A predefined region is a localized area on a substrate that is, was, or is intended to be used for the formation of a specific material. The predefined region may be referred to, in the alternative, as a "known" region, a "reaction" region, a "selected" region, or simply a "region." The predefined region may have any convenient shape, e.g., linear, circular, rectangular, elliptical, or wedge-shaped. Additionally, the predefined region can be a bead or pellet which is coated with the component(s) of interest. In this embodiment, the bead or pellet can be identified with a tag, such as an etched binary bar code, that can be used to identify which components were deposit on the bead or pellet. The area of the predefined regions depends on the application and is typically smaller than about 25 $cm^2$. However, the predefined regions may be smaller than 10 $cm^2$, smaller than 5 $cm^2$, smaller than 1 $cm^2$, smaller than 1 $mm^2$, smaller than 0.5 $mm^2$, smaller than 10,000 $\mu m^2$, smaller than 1,000 $\mu m^2$, smaller than 100 $\mu m^2$, or even smaller than 10 $\mu m^2$.

Radiation

Radiation refers to energy with a wavelength between $10^{-14}$ and $10^4$. Examples of such radiation include electron beam radiation, gamma radiation, x-ray radiation, ultraviolet radiation, visible light, infrared radiation, microwave radiation, and radio waves. Irradiation refers to the application of radiation to a surface.

Component

Component is used herein to refer to each of the individual substances that are deposited onto a substrate. Components can act upon one another to produce a particular material. Components can react directly with each other or with an external energy source such as radiation, an electric field, or a magnetic field. A third material or a chemical substance can also act upon components. A component can be an element, a chemical, a material, or a mixture of elements and chemicals. Components can form layers, blends or mixtures, or combinations thereof.

Source Material

The term source material is used herein to refer to the original material from which a component was derived. Source materials can be composed of elements, compounds, chemicals, molecules, etc. that are dissolved in a solvent, vaporized, evaporated, boiled, sublimed, ablated, etc., thus allowing the source materials to deposit onto a substrate during the synthesis process.

Resulting Material

The term resulting material is used herein to refer to the component or combination of components that have been deposited onto a predefined region of a substrate. The resulting materials may comprise a single component, or a combination of components that have reacted directly with each other or with an external source. Alternatively, the resulting material may comprise a layer, blend or mixture of components on a predefined region of the substrate. The resulting materials are screened for specific properties or characteristics to determine their relative performance.

Mixture or Blend

The term mixture or, interchangeably, blend refers to a collection of molecules, ions, electrons, or chemical substances. Each component in the mixture can be independently varied. A mixture can consist of two or more substances intermingled with no constant percentage composition, wherein each component may or may not retain its essential original properties, and where molecular phase mixing may or may not occur. In mixtures, the components making up the mixture may or may not remain distinguishable from each other by virtue of their chemical structure.

Layer

The term layer is used herein to refer to a material that separates one material, component, substrate or environment from another. A layer is often thin in relation to its area and covers the material beneath it. A layer may or may not be thin or flat, but once it is deposited it generally covers the entire surface such that it separates the component or substrate below the layer from the component or environment above the layer.

Heterogeneous catalysts

Heterogeneous catalysts enable catalytic reactions to occur with the reactants and catalysts residing in different phases. As used herein, heterogeneous catalysts include, but are not limited to, mixed metal oxides, mixed metal nitrides, mixed metal sulfides, mixed metal carbides, mixed metal fluorides, mixed metal silicates, mixed metal aluminates, mixed metal phosphates, nobel metals, zeolites, metal alloys, intermetallic compounds, inorganic mixtures, inorganic compounds, and inorganic salts.

Homogeneous catalysts

Homogeneous catalysts enable catalytic reactions to occur with the reactants and catalysts residing in the same phase. As used herein, homogeneous catalysts include, but are not limited to, catalysts for the polymerization of one or more olefinic or vinyl monomers. The olefinic monomers include, but are not limited to, ethylene or alpha-olefins containing from 3 to 10 carbon atoms, such as propylene, 1-butene, 1-pentane, 1-hexene, and 1-octene. The vinyl monomers include, but are not limited to, vinyl chloride, vinyl acetate, vinyl acrylate, methylmethacrylate, methyl vinyl ether, ethyl vinyl ether and acetonitrile. The catalysts employed to carry out a polymerization of one or more monomers of this type include, but are not limited to, radical catalysts, cationic catalysts, anionic catalysts, and anionic coordination catalysts.

Generating Arrays of Materials

Generally, an array of materials is prepared by successively delivering components of the materials to predefined regions on a substrate, and simultaneously reacting the components to form at least two materials or, alternatively, the components are allowed to interact to form at least two materials. In one embodiment, for example, a first component of a first material is delivered to a first predefined location on a substrate, and a first component of a second material is delivered to a second predefined region on the same substrate. Simultaneously with or thereafter, a second component of the first material is delivered to the first region on the substrate, and a second component of the second material is delivered to the second region on the substrate. Each component can be delivered in either a uniform or gradient fashion to produce either a single stoichiometry or, alternatively, a large number of stoichiometries within a single predefined region. Moreover, the components can be delivered as amorphous films, epitaxial films or lattice or superlattice structures. The process is repeated, with additional components, to form a vast array of components at predefined locations on the substrate. Thereafter, the components are simultaneously reacted to form at least two materials or, alternatively, the components interact to form at least two materials. As described herein, the components can be sequentially or simultaneously delivered to the predefined regions on the substrate using any of a number of different delivery techniques.

Numerous combinatorial techniques can be used to synthesize the various arrays of diverse materials on the substrate according to the present invention. For example, in one embodiment a first component of a first and second material is delivered to the predefined regions on the substrate. Then a second component of the first and second materials is delivered to the predefined regions on the substrate. This process continues for the other components (e.g., third, fourth, fifth, etc. components) and/or the other materials (e.g., third, fourth, fifth, etc. materials) until the array is complete. In another embodiment, the array is formed as previously described, but the resulting materials are formed immediately as the components contact each other on the substrate. In yet another embodiment, the array is formed as previously described, but after the various components are delivered to the substrate, a processing step is carried out which allows or causes the components to interact to form layers, blends, mixtures, and/or materials resulting from a reaction between components. In still another embodiment, two or more components are delivered to the predefined regions on the substrate using fast sequential or parallel delivery techniques such that the components interact with each other before contacting the substrate. The resulting array of materials, each at a discrete and known location on the substrate, comprises layers, blends, mixtures, and/or materials resulting from a reaction between components.

Essentially, any conceivable substrate can be employed in the invention. The substrate can be organic, inorganic, biological, nonbiological, or a combination thereof. The substrate can exist as particles, strands, precipitates, gels, sheets, tubing, spheres, containers, capillaries, pads, slices, films, plates, slides, etc. The substrate can have any convenient shape, such as a disc, square, sphere, circle, etc. The substrate is preferably flat, but may take on a variety of alternative surface configurations. For example, the substrate may contain raised or depressed regions on which the synthesis of diverse materials takes place. The substrate and its surface preferably form a rigid support on which to carry out the reactions described herein. The substrate may be any of a wide variety of materials including, for example, polymers, plastics, pyrex, quartz, resins, silicon, silica or silica-based materials, carbon, metals, inorganic glasses, inorganic crystals, and membranes. Upon review of this disclosure, other substrate materials will be readily apparent to those of skill in the art. Surfaces on the solid substrate can be composed of the same materials as the substrate or, alternatively, they can be different (i.e., the substrates can be coated with a different material). Moreover, the substrate surface can contain thereon an adsorbent (for example, cellulose) to which the components of interest are delivered. The most appropriate substrate and substrate-surface materials will depend on the class of materials to be synthesized and the selection in any given case will be readily apparent to those of skill in the art. In other embodiments, the substrate can be a series of small beads or pellets. As with the single substrate having an array of materials thereon, each of the individual beads or pellets can be screened for materials having useful properties.

A variety of substrate systems are possible, including two- and three-dimensional substrate systems. In some embodiments, the two-dimensional combinatorial catalysis library will be deposited either on a porous substrate, such as alumina, or on a non-porous substrate. In some embodiments, the substrate will further contain a synthesis support. The synthesis support can be made of alumina, silicon, quartz, zeolites, Teflon, silica and other oxides, etc. The synthesis support may be in the form of beads, discs or any other geometry in, for example, one of the following substrate configurations: i) a porous support placed in wells wherein the reactants flow through the support from the top of the wells out through a hole in the bottom of the wells (or flow may be in the reverse direction); ii) a porous support placed in wells wherein the reactants do not flow through from the top to the bottom of the wells, but only to and from the top of the wells; iii) a non-porous support placed in wells wherein the reactants flow around the support from the top of the wells out through a hole in the bottom of the wells (or flow may be in the reverse direction); iv) a non-porous support placed in wells wherein the reactants do not flow through from the top to the bottom of the wells, but only to and from the top of the wells; or v) a porous or non-porous support not contained in wells wherein the reactants are deposited directly onto the substrate surface.

For instance, in one possible configuration illustrated in FIG. 1, a sample chamber (not shown) is filled with reactant gas A at a pressure P. Focused IR heating from source 103 selectively activates individual catalyst elements 101 contained on an array substrate 105. Alternatively, resistive heating elements (not shown) can be incorporated into substrate 105. All of the library elements 101 are in contact with reactant gas A; however, only when heated will the catalyst posses significant activity to produce appreciable products. If necessary the library can be cooled to avoid any side reactions.

Figure 2:
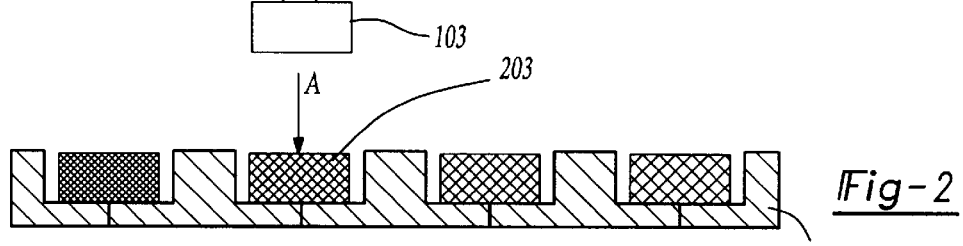
FIG. 2 illustrates a permeable substrate according to the invention, wherein a reactant gas is driven through a supported library.

In a second possible configuration illustrated in FIG. 2, a permeable substrate 201 is utilized. Thus reactant gas A at a pressure P on top of the library is driven through the supported catalyst library element 203 and then both unreacted reactants and products pass through the porous substrate into a region of lower pressure 205 where the products are detected. The flow can be directed though one element path at a time by sealed conduits or, alternatively, it can be directed through all elements simultaneously. Individual elements can be selectively heated for serial measurement of the products or the entire library heated for parallel characterization (e.g., optical emission imaging). This method has the advantage that the pressure drop across the substrate allows the gas detection system to sample a lower pressure stream. In the case of liquid or solid phase products, volatile components of the products can be sampled identically to the gas phase products. For products with insufficient vapor pressure, scanned infrared laser heating or individual resistive element heating configurations can be used.

Generally, physical masking systems can be employed in combination with various deposition techniques in order to apply components onto a substrate in a combinatorial fashion, thereby creating arrays of resulting materials at predefined locations on the substrate. The arrays of resulting materials will usually differ in composition, stoichiometry and/or thickness across the substrate. The components can, for example, be dispensed to the substrate in the form of a gas, a liquid or a powder. Suitable deposition techniques include, but are not limited to, sputtering, electron-beam and thermal evaporation, laser deposition, ion beam deposition, chemical vapor deposition, and spray-coating. In solution phase deposition techniques include, for example, sol/gel methods, discrete liquid dispensing techniques (e.g. pipettes, syringes, ink jets, etc.), spin coating with lithography, microcontact printing, spraying with masks and immersion impregnation. Moreover, such dispenser systems can be manual or, alternatively, they can be automated using, for example, robotics techniques. A more complete description of representative arrays of materials and systems and methods for generating such arrays of materials can be found in commonly assigned, co-pending patent applications "The Combinatorial Synthesis Of Novel Materials", Publication No. WO 95/13278, filed Oct. 18, 1995; "Systems and Methods for the Combinatorial Synthesis of Novel Materials," patent application Ser. No. 08/841,423, filed Apr. 22, 1997; and "Discovery of Phosphor Materials Using Combinatorial Synthesis Techniques," provisional patent application Ser. No. 60/039,882, filed Mar. 4, 1997; the complete disclosures of which are incorporated herein by reference for all purposes.

In some embodiments of the present invention, after the components have been deposited onto predefined regions on a substrate, they are reacted using a number of different techniques. For example, the components can be reacted using solution based synthesis techniques, photochemical techniques, polymerization techniques, template directed synthesis techniques, epitaxial growth techniques, by the sol-gel process, by thermal, infrared or microwave heating, by calcination, sintering or annealing, by hydrothermal methods, by flux methods, by crystallization through vaporization of solvent, etc. Furthermore, each predefined region on the substrate can be heated simultaneously or sequentially using heat sources such as focussed infrared radiation, resistive heating, etc. Reactants can, for example, be dispensed to the library of elements in the form of a gas or a liquid. Other useful techniques that can be used to react the components of interest will be readily apparent to those of skill in the art. Additionally, components can react with each other instantly, upon contacting each other, or in the air before contacting the substrate. The components can also form layers, blends or mixtures, in the air or on the substrate, rather than reacting with each other.

Once prepared, the array of resulting materials can be screened for useful properties using the methods described herein. Either the entire array or, alternatively, a section thereof (e.g., a row of predefined regions) can be screened using parallel or fast sequential screening. In some embodiments, a predefined region on the substrate and, therefore, the area upon which each distinct material is synthesized, is smaller than about 25 cm$^2$, less than 10 cm$^2$, less than 5 cm$^2$, less than 1 cm$^2$, less than 1 mm$^2$, or less than 0.5 mm2. In other embodiments, the regions have an area less than about 10,000 $\mu$m$^2$, less than 1,000 $\mu$m$^2$, less than 100 $\mu$m$^2$, or less than 10 $\mu$m$^2$. Accordingly, the density of regions per unit area will be greater than 0.04 regions/cm$^2$, greater than 0.1 regions/cm$^2$, greater than 1 region/cm$^2$, greater than 10 regions/cm$^2$, or greater than 100 regions/cm$^2$. In other embodiments, the density of regions per unit area will be greater than 1,000 regions/cm$^2$, greater than 10,000 regions/cm$^2$, greater than 100,000 regions/cm$^2$, or greater than 10,000,000 regions/cm$^2$.

In some embodiments, the screening systems of the present invention will be used to screen a single substrate having at least 9 different materials. In other embodiments, the screening system scans a single substrate having more than 50, 100, 10$^3$, 10$^4$, 10$^5$, 10$^6$, or more materials synthesized thereon. In some embodiments, the substrate will comprise arrays of materials with as few as two components, although the substrate can have materials with 3, 4, 5, 6, 7, 8 or more components therein. The substrate can be screened for materials having useful properties and/or the resulting materials can be ranked, or otherwise compared, for relative performance with respect to useful properties or other characteristics. Resulting materials include, but are not limited to, covalent network solids, ionic solids and molecular, inorganic materials, intermetallic materials, metal alloys, ceramic materials, organic materials, organometallic materials, non-biological organic polymers, composite materials (e.g., inorganic composites, organic composites, or combinations thereof), or homogeneous or heterogeneous catalysts. Again, once useful resulting materials have been identified using the methods of the present invention, a variety of different methods can be used to prepare such materials on a large or bulk scale with essentially the same structure and properties. Properties which can be screened for include, but are not limited to, electrical, thermal, mechanical, morphological, optical, magnetic, chemical, conductivity, super-conductivity, resistivity, thermal conductivity, anisotropy, hardness, crystallinity, optical transparency, magnetoresistance, permeability, frequency doubling, photoemission, coercivity, dielectric strength, or other useful properties which will be apparent to those of skill in the art upon review of this disclosure. Importantly, the synthesizing and screening of a diverse array of resulting materials enables new compositions with new physical properties to be identified.

Given the chemical complexity of catalytic systems, the lack of predictive models, the number of possible combinations of metals, counterions, ligands, and supports, and the time consuming process of evaluating the performance of each catalyst formulation utilizing conventional laboratory pilot reactors, it is not surprising that the search for the optimum catalyst is a time consuming and inefficient process. Thus, a combinatorial approach to the discovery and optimization of catalytic systems, which combines the synthesis of catalyst libraries with the screening tools of this invention, is useful for accelerating the pace of research in this field. The catalyst libraries of the present invention can include organic (e.g., catalytic antibodies), organometallic, heterogeneous or solid state inorganic array elements. Organometallic catalyst libraries which can be screened for useful catalytic properties include, but are not limited to, those described in co-pending U.S. patent application Ser. No. 08/898,715, filed Jul. 22, 1997, which is hereby incorporated by reference for all purposes.

Catalyst libraries comprising inorganic (e.g., heterogeneous and solid state inorganic) materials can also be screened for useful properties using the methods of this invention. Catalyst libraries can comprise powders, impregnated solid supports, inorganic films and monoliths, or crystals that are spatially separated within a substrate system (e.g., wells, flat surfaces). Solid state inorganic materials useful as heterogeneous catalysts are well known in the chemical industry. Heterogeneous catalysts enable catalytic reactions to occur with the reactants and catalysts residing in different phases and include, but are not limited to, mixed metal oxides, mixed metal nitrides, mixed metal sulfides, mixed metal carbides, mixed metal fluorides, mixed metal silicates, mixed metal aluminates, mixed metal phosphates, nobel metals, zeolites, metal alloys, intermetallic compounds, inorganic mixtures, inorganic compounds, and inorganic salts. Heterogeneous catalyst systems typically comprise metals, metal oxides, metal sulfides, and other metal salts, can be supported on a carrier (e.g., alumina, silica of controlled particle size and porosity), and can be used in bulk.

Heterogeneous catalysts can be prepared by a number of methods which are well known in the art and include mixing reactive solutions, impregnation of solutions of metal salt precursors onto or into solid carriers, coprecipitation, and mixing colloidal dispersions. These methods yield chemically complex, multicomponent solid products that can be further treated with reducing agents, oxidizing agents and other third components and modifiers to produce optimized materials.

Once an array of catalysts is formed, the screening methods of the present invention can be used to characterize the catalytic properties of the various compounds by observing, for example, activity, lifetime and selectivity for a variety of catalytic transformations. For purposes of this invention, a catalyst is defined as any material that accelerates the rate of a chemical reaction and which is either not consumed during the reaction or which is consumed at a rate slower (on a molar basis) than the reaction that is being catalyzed. Examples of catalytic reactions/transformations include, but are not limited to, total oxidations (e.g., the conversion of CO into $CO_2$ using oxygen, or $NO_x$ for simultaneous reduction of the $NO_x$), selective oxidations (e.g., epoxidations of olefins), reductions (e.g., hyrdogenation of unsaturated species), polymerizations (e.g., ethylene copolymerizations), dimerization (e.g., ethylene to butene), trimerization, oligomerization, decompositions (e.g., conversion of $NO_x$ into $N_2$ and $O_2$), hydrosilation, carbonylations, hydrocynation, hydroformylation, isomerization, metathesis (e.g., of olefins and acetylenes), carbon-hydrogen activation, cross coupling, Friedel-Crafts acylation and alkylation, hydration, and Diels-Alder reactions.

Detailed Description of a Scanning Mass Spectrometer

Figure 3:
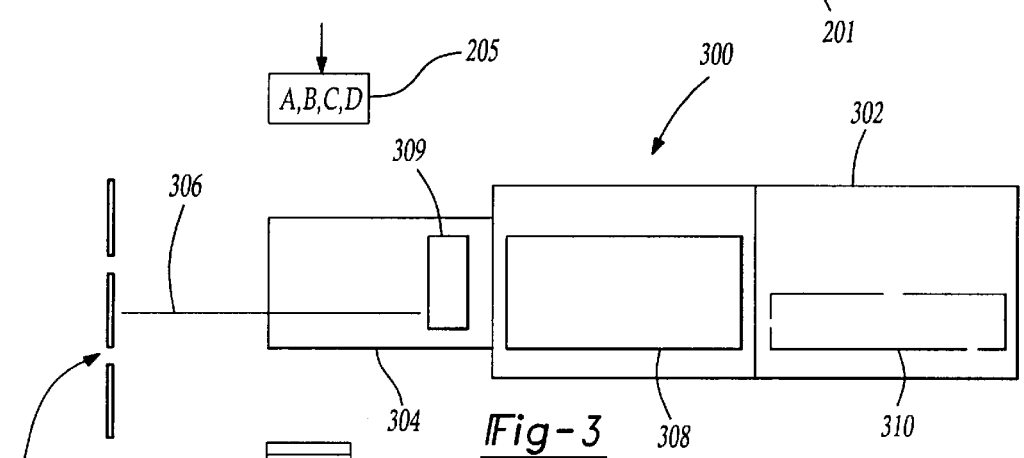
FIG. 3 schematically illustrates the basic components of a mass spectrometers according to the present invention.

FIG. 3 schematically illustrates the basic components of the mass spectrometers of the present invention. As shown, a quadrupole mass spectrometer 300 comprises a housing 302, an ionization chamber 304, and a conduit system 306. Conduit system 306 is typically a sampling probe that is used to draw materials (e.g., gases) from a substrate 307 into the ionization chamber 304. An ion source 309 converts the gas or gases into charged species of a certain mass-to-charge (m/z) ratio.

Ion source 309 may be an electron beam at one end of the ionization chamber 304 which collide with, and ionize, the gas molecules in the chamber. Alternatively, photons of specific energies may be used (photoionization) to generate ions of selected molecules. Some of these ions are then accelerated through a channel, past a mass filter or an ion guide 308. Ion guide 308 preferentially blocks ions of an undesired m/z ratio, allowing unblocked ions to reach a quadrupole mass detector 310 positioned at the other end of housing 302. The ions that impact upon the collector surface within mass detector 310 generate a current signal proportional to the number of ions and thus proportional to the population of gas molecules. The mass spectrum is useful for both identifying and quantifying the sample. The collector is connected to an external circuit (not shown) to amplify the signal that is proportional to the amount of gas ions impacting on the collector surface.

Conduit system 306 typically includes at least one sampling probe in which the distal end of the probe is positioned over a specific library element or region on the substrate array. The proximal end of the probe is terminated at or within the ionization chamber. The sampling probe typically has an opening on the order of 0.01 mm to 0.5 mm and, more preferably, 0.05 mm to 0.2 mm. In some embodiments the conduit system comprises an array of conduits or probes, each having a distal end positioned adjacent to a predefined location on the substrate and a proximal end coupled to the ionization chamber. In these embodiments each probe has a valve allowing fluids to be drawn sequentially from the predefined locations. In other embodiments the conduit system comprises a single conduit or sample probe positioned over a single predefined location on the substrate. A translation stage moves the sample probe across the substrate, or the translation stage moves the substrate relative to the conduit, thus allowing a plurality of the predefined locations to be sequentially scanned.

Quadrupole mass detector 310 is usually capable of detecting a one-part-per-million (1 ppm) component in one atmosphere background pressure. To increase this detection range to $10^8$, ions of the product, reactant, and other molecules are filtered by quadrupole ion guide 308 positioned between ionization chamber 304 and quadropole mass detector 310. Preferably, ion guide 308 provides two orders of magnitude of purification, only passing a concentrated beam of the ions of interest to mass detector 310.

Figure 4:
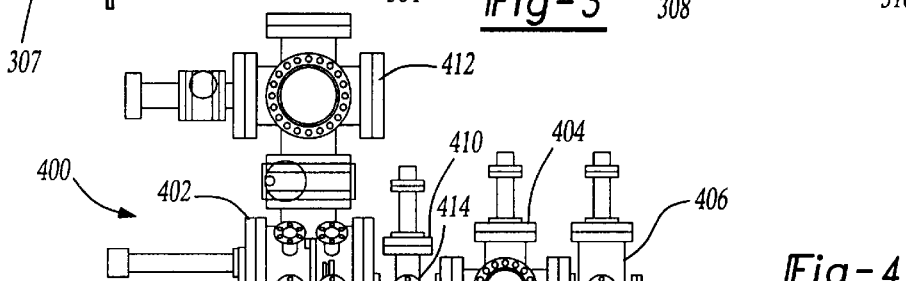
FIG. 4 is a side view of a specific embodiment of a scanning mass spectrometer according to the present invention.

FIGS. 4–6 provide a side, top, and front view, respectively, of a three-stage differentially pumped vacuum system 400. System 400 generally includes a reaction chamber 402, an ion guide or mass filter 404, a quadrupole mass spectrometer 406 which includes a mass detection chamber or collector (not shown), and an ionizer or QMS cross 410. Although ion guide 404 and quadrupole mass spectrometer 408 can be operated at a pressure of $10^{-5}$ torr for normal operations, the differential pumping eliminates the possible ion-molecule reactions in these regions and guarantees a high dynamic range. As shown, reaction chamber 402, ionizer 410, ion guide 404, and mass spectrometer 406 are mounted on a support frame 408. Reaction chamber 402 houses the substrate and the sampling probe (not shown in FIGS. 4–6). Reaction chamber 402 may also include a translation stage for moving the substrate relative to the sampling probe for scanning across the substrate. A source chamber 412 is coupled to the top of reaction chamber 402 for supplying reactant gases to the substrate. Source chamber 412 includes a preparation chamber (not shown) that may be used for pretreating the library with reactant gases, e.g., catalysts.

The sampling probe within reaction chamber 402 is coupled to ionizer 410 by a conduit 414. Ionizer 410 includes an inner ionization zone or chamber (not shown) for ionizing gas products drawn from the substrate. After being ionized, the reactant gases pass through ion guide 404 and into mass spectrometer 406. A filament coil (not shown) is positioned within ionization chamber and formed from a suitable filament material, such as tungsten or iridium, by conventional filament winding techniques. The filament coil provides a source of electrons to ionize gas molecules for detection by the collector. Other ion sources may also be used in alternative embodiments. In addition, spectrometer 406 may be used to detect naturally occurring ions.

Spectrometer 406 includes a collector (not shown) that provides a measurement of the flux of mass-filtered ions of the selected m/z ratio exiting from the ion guide. If desired, a mass spectrum can be generated by scanning the RF and DC voltages and measuring the transmitted ion current at each setting. The collector includes several lenses mounted in the channels of the quadrupole which further tune the quadrupoles, thus permitting only ions having the requisite m/z ratio to reach the surface of the collector. For example, an entrance lens (not shown) permits only those ions traveling towards the collector in substantially the center of the channels to actually enter the collector.

Computer controlled power supply electronics provide all of the necessary voltages to operate the mass spectrometer system. An amplifier and analog-to-digital converter registers the detector signal, which is subsequently processed by the computer for data analysis and display.

FIG. 7 illustrates the inner portion of reaction chamber 402 in one embodiment of the present invention. As shown, a wafer 702 is positioned within chamber 402 on a susceptor 704 and underneath a fluid probe 706. Wafer 702 can be moved relative to probe 706, for example through the use of a translation stage as discussed below. In the preferred embodiment probe 706 is stationary while susceptor 704, and therefore wafer 702, are movable in at least the x and y directions. In this embodiment the catalytic reactions occur within reaction chamber 402, and the product gases are removed from chamber 402 into the remainder of mass spectrometer system 400.

FIGS. 8–10 provide a detailed illustration of a conduit system 800. In this embodiment, conduit system 800 includes a single sampling probe 802. Preferably the substrate is moved relative to sampling probe 802 by a translation stage (not shown), thus allowing sequential scanning of predefined regions on the substrate. Conduit system 800 also includes a gas inlet conduit 804 and a gas outlet conduit 806. Conduits 804 and 806 as well as probe 802 pass through a reaction chamber flange 808.

FIG. 9 is an expanded cross-sectional view of sampling probe 802. Gas inlet conduit 804 includes an inner passage 904 coupled to an inner passage 906 of probe 802. Passage 904 delivers gas, such as a reactant gas, to a library element or predefined location on a substrate (not shown) located at the distal end of probe 802. Gas outlet conduit 806 is coupled to sampling probe 802 by a reducing elbow 910 and an outer passage 908. Outer passage 908 is concentric with, and separate from, inner passage 906.

FIG. 10 provides further detail regarding the distal end of probe 802. Probe 802 tapers down to a capillary sized conduit 1000. At the end of conduit 1000 is a pinhole opening 1002 on the order of 0.02 mm to 0.2 mm in diameter, preferably about 0.03 to 0.04 mm in diameter, which is positioned over the substrate (not shown). Similarly, concentric outer passage 908 tapers down to a small annular opening 1004.

In use, reactant gases are delivered from source chamber 412 through passages 904 and 906 of inlet conduit 804 and sampling probe 802, and onto a predefined region on the substrate. The reactant gases react with the material(s) at the predefined region to form one or more gas products. The gas products are then drawn back through passage 906 of sample probe 802 to reaction chamber 402. Sampling probe 802 is isolated from gas inlet conduit 804 so those gas products will not pass through inlet conduit 804. The remaining reactant gases are subsequently removed through concentric outlet passage 908 to gas outlet conduit 806, where they are expelled.

Referring to FIG. 11, a translation stage 1100 includes a sample holder 1102 for mounting substrate 702 at the center of translation stage 1100. Translation stage 1100 includes drive motors (not shown) for moving sample holder 1102 and substrate 702 in XYZ directions. Stage 1100 has a travel dimension of about 5 to 13 cm such that sampling probe 802 may access any location on a 7.6 cm diameter substrate. Of course, substrate 702 may have different sizes and translation stage 1100 may be modified for use with larger or smaller substrates. Stage 1100 preferably has a 10 $\mu$m accuracy in all three directions.

Figure 12:
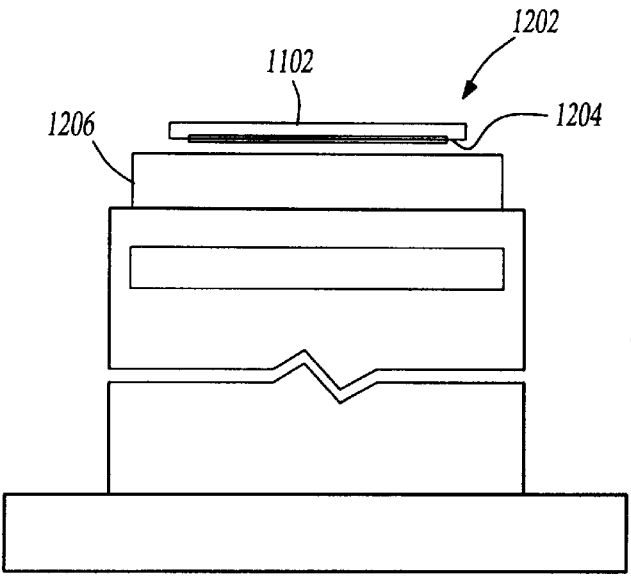
FIG. 12 illustrates a heat transfer system of a scanning mass spectrometer according to the present invention.

Referring to FIG. 12, system 400 further includes a heat transfer system 1202 positioned below sample holder 1102 for transferring heat to and from substrate 702 (not shown). To that end, sample holder 1102 has a clear lower surface 1204 to facilitate heating and temperature monitoring of substrate 702. As shown, heat transfer system 1202 includes a flat heater 1206 separated from substrate 702 by about 2 to 3 mm. Flat heater 1206 is preferably configured to selectively heat predefined locations on the substrate so that sampling probe 802 can sequentially scan these locations.

Figure 13:
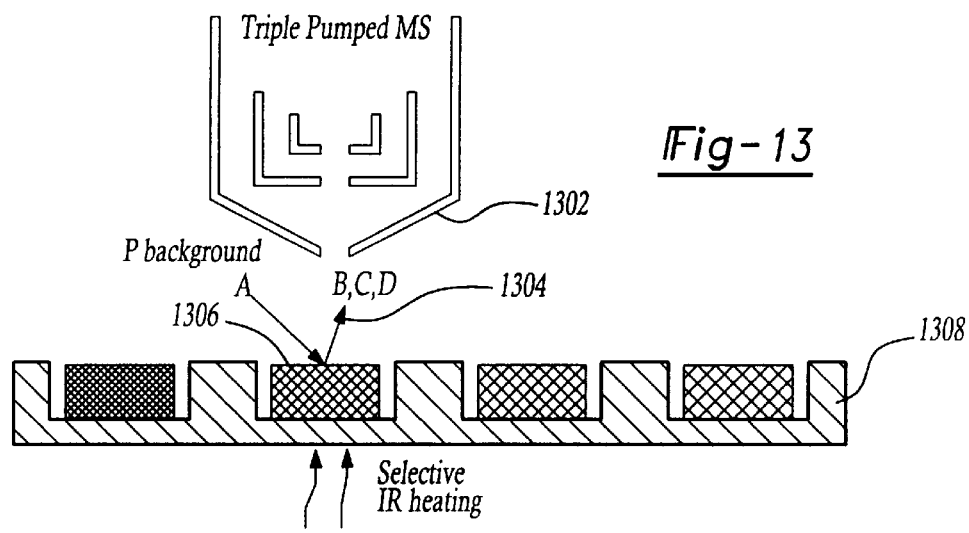
FIG. 13 illustrates a method of employing a differentially pumped mass spectrometer for sampling a product stream or volume surrounding a library compound.
Figure 14:
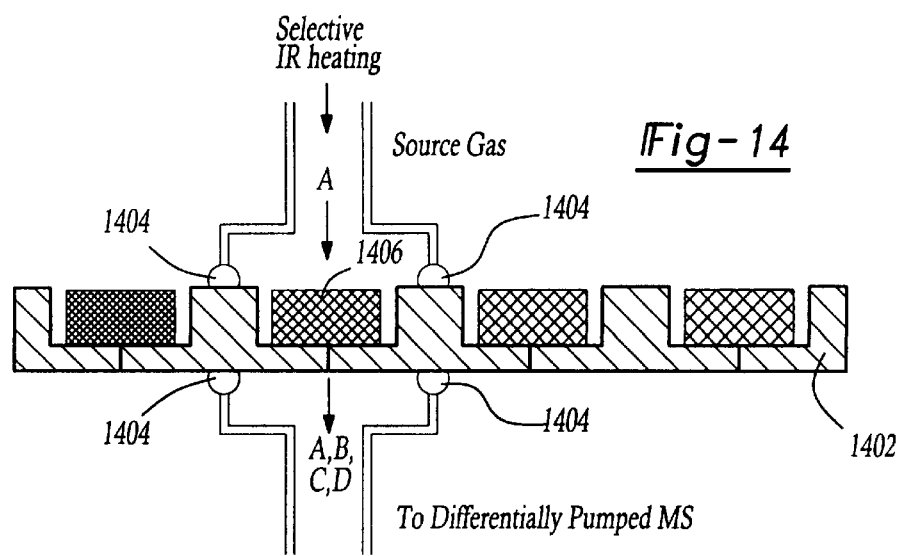
FIG. 14 illustrates a second method of employing a differentially pumped mass spectrometer for sampling a product stream or volume surrounding a library compound.

FIGS. 13 and 14 schematically illustrate the use of a differentially pumped mass spectrometer such as the one described above. As shown in FIG. 13, a highly sensitive, species dependent probe 1302 samples a product stream 1304 of a library compound 1306 on a substrate 1308. This approach requires that sampling probe 1302 be carefully positioned over the element, or the exit stream, to be analyzed. A spatially controllable heater (e.g., a scannable heat source or an individual resistive heater) achieves the thermal control of each library element (e.g., element 1306). The spectrometer may sample the products of this heat reaction, or the products of a reaction with reactant gases delivered through the sample probe as discussed above.

In an alternative embodiment illustrated in FIG. 14, substrate 1402 is physically scanned in front of a fixed heating source-detector nozzle or through fixed inlet and outlet tubes that are sealed against the substrate at locations 1404, thus isolating each individual library element 1406. Alternatively, the substrate can be fixed and the detector assembly and heater scanned.

Library Positioning System

Figure 15:
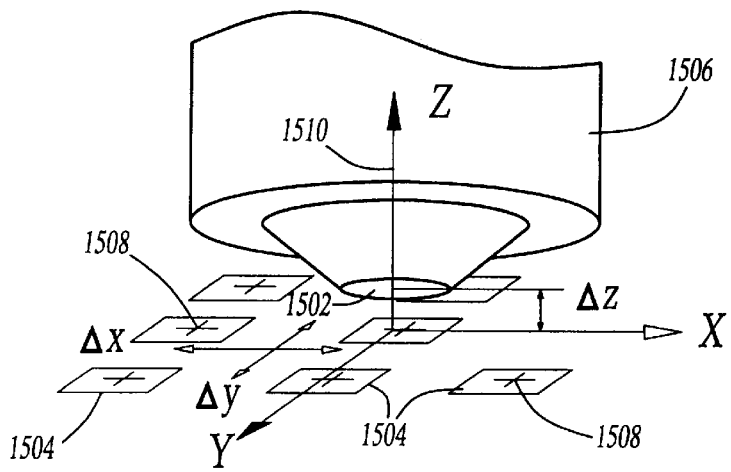
FIG. 15 illustrates the relative arrangement of the library elements and a scanning mass spectrometer probe according to one embodiment of the invention.

FIG. 15 is illustrates an arrangement of library elements relative to the scanning mass spectrometer sampling probe. A XYZ coordinate system is selected so that the XY-plane is parallel to a sample probe surface 1502 and the sample probe symmetry axis passes through the origin. The center of sample surface 1502 has a constant negative Z-displacement from the origin ($\Delta z$). The repetitive dimensions of library elements 1504 are $\Delta x$ and $\Delta y$ in the XY-plane, respectively. Thus the positioning problem is how to align the center, 1508, of each library element 1504 to the center, 1510, of sampling surface 1502 while maintaining a constant spacing, $\Delta z$, between the element surface and the sample probe surface. One solution to this problem is described below.

Figure 16:
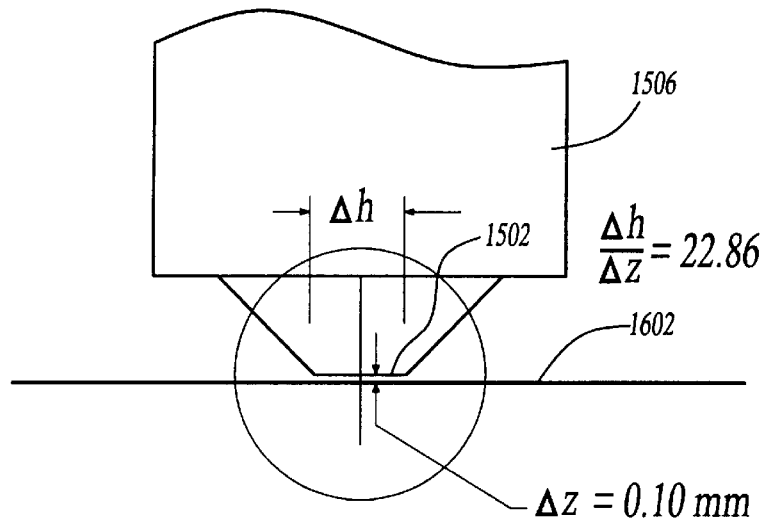
FIG. 16 illustrates the laboratory XYZ coordinate space used to resolve the positioning problem.

The first step in resolving the positioning problem is to define a laboratory coordinate system, XYZ, as illustrated in FIG. 16. The x- and y- axes are parallel to the x and y manipulators, respectively. The z-axis is along the system's symmetry axis pointing from the reaction chamber to the mass spectrometer. The origin of the coordinates is located at the center of the library element as if it were under experimentation.

After a library element 1602 is loaded on the XYZ translation stage, it is pushed in the z-dimension to establish a distance, $\Delta z_0$, of 0.10 mm from sample probe surface 1502 to element surface 1602. The distance between element surface 1602 and sample probe surface 1502 is detected by a CCD camera (z-camera) imaging in a direction normal to the wafer surface or the symmetry axis of the sample probe. By using the diameter, $\Delta h$, of the outer-most sample probe surface as a reference, the distance can be precisely measured. When a ratio of the diameter, $\Delta h$, to the distance, $\Delta z$, equals 22.86, the distance is the desired 0.10 mm.

Figure 17:
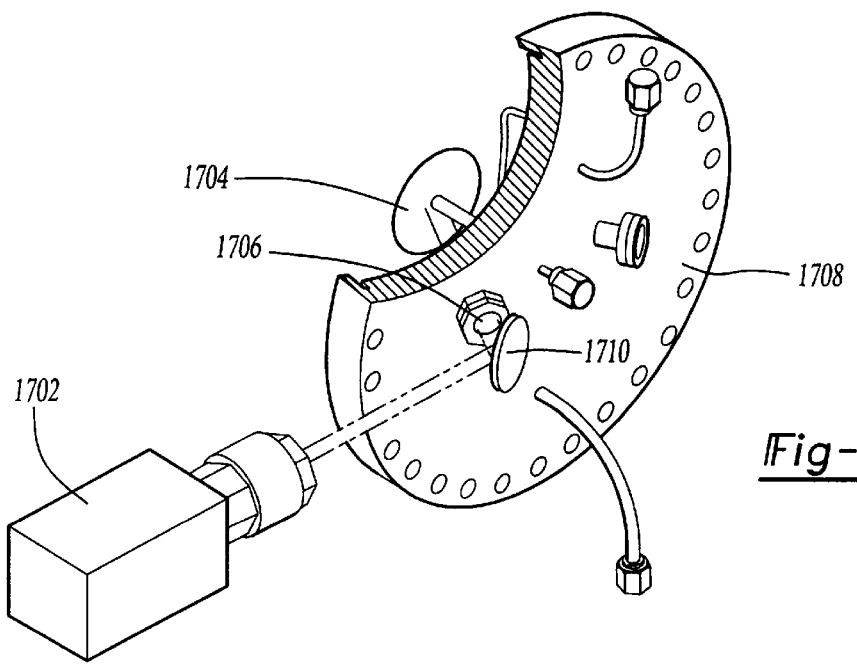
FIG. 17 illustrates the location of a XY-position CCD camera in relation to a substrate.
Figure 18:
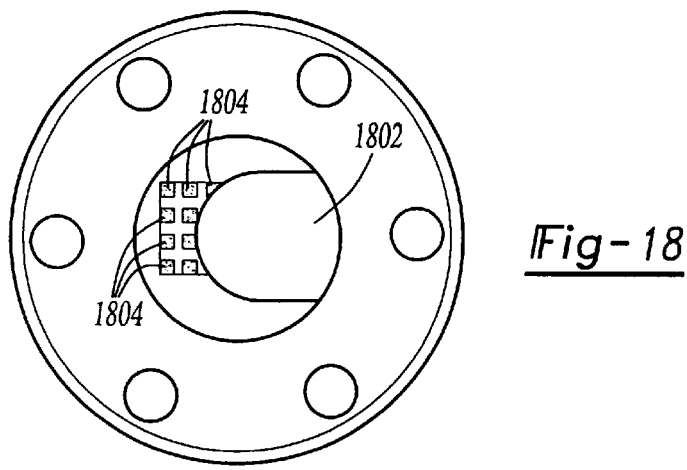
FIG. 18 illustrates the view by the camera shown in FIG. 17.

FIG. 17 illustrates one embodiment of the invention in which a camera 1702 views sample 1704 via a window 1706 mounted in an interface flange 1708. Preferably a turning mirror 1710 is used so that camera 1702 may be placed off-axis as shown. FIG. 18 illustrates the view by camera 1702. Although it is typically not possible to view the library element directly under sample probe 1802, the neighborhood elements 1804 can be used as references.

EXAMPLE

The following example illustrates a method for screening heterogeneous catalyst libraries with a scanning mass spectrometer according to the present invention. This example is offered for illustrative purposes and is not intended to limit the invention in any manner. Those of skill in the art will readily recognize a variety of non-critical parameters that can be changed or modified to yield essentially the same result.

Traditionally, industrial catalysts are characterized by the use of micro-reactors that contain up to grams of porous-supported catalysts. With the introduction and proliferation of combinatorial techniques into materials synthesis, the number of potential new catalysts and/or variations of existing catalysts are expected to increase dramatically in the next few years. Traditional micro-reactor-based testing techniques are limited in measurement time (from minutes to hours, even days) and material quantity (typically up to a few grams) and therefore cannot meet the demands for high-throughput screening required by combinatorially-generated catalysts.

In order to analyze the residence time and dynamic range required for the mass spectrometer, a hypothetical catalyst is used as an example. The hypothetical catalyst is assumed to be capable of converting 80% of reactant A to product B in the presence of co-reactant C. The reaction is assumed to be a first-order reaction for both reactants A and C, which are in contact with the catalyst for 1 second. In a typical differential micro-reactor, and assuming conditions comparable to those used in many industrial catalytic screening processes, the surface area of the catalyst is 2 m$^2$ and the reaction is carried out at a pressure of 20 atmospheres.

In one embodiment of the invention, the reaction is carried out at one atmosphere for 1 second over a catalyst element with a surface area of 1 mm by 1 mm. The catalyst element has approximately 50% of the reactivity of the above hypothetical catalyst. The conversion ratio for one second of residence time over 1 mm$^2$ of such a catalyst is on the order of 10 ppb.

In order to expose 1 mm$^2$ surface of catalyst for 1 second with a reaction gas mixture, a cylindrical volume of pseudo-static reaction chamber is employed. As illustrated in FIGS. 8–10, a thin, elongate capillary of a sampling probe connects a reaction volume to the ionization zone of the mass spectrometer. As previously described, inner tube 906 provides a reaction gas in the vicinity of the catalyst and outer concentric tube 908 removes reaction gas from the system to prevent contamination (to other catalyst elements). The probe has a reaction volume of 0.39 mm/m$^3$ covering a surface area of 0.785 mm$^2$ (i.e., 1 mm diameter).

The capillary in this embodiment has a 50 $\mu$m inner diameter and is 30 cm long. The internal volume of the capillary is 0.6 $\mu$l. One end of the capillary is exposed to one atmosphere pressure of reaction gas mixture while the other end is at a pressure less than 10$^{-4}$ torr. Gas flow in the capillary changes from viscous flow to molecular flow. The throughput of the capillary can be calculated using the following integration equation based on Knudsen's theory:

$$\frac{Q}{C_m \overline{P}_i} = \frac{1}{2}\delta^2 + \frac{17}{21}\delta + 9 \times 10^{-3} \times \ln(1 + 21 \times \delta)$$

in which the average pressure over that at both ends is given by:

$$\delta = \frac{\overline{P}D}{\overline{P}_i D}$$

and where D is the diameter of the capillary tubing, Q is the throughput, and $C_m$ is the molecular flow conductance. At 20° C., $\overline{P}_i D = 6.7 \times 10^{-2}$ Torr cm for air. Therefore the throughput for the capillary is $2.95 \times 10^{-4}$ torr l/s. At one atmosphere, the capillary can accept 0.39 ml/s. Since the volume of the reaction zone is 0.39 ml, the residence time is 1 second as required for the 10 ppb conversion ratio. The total molecular flux is $1.1 \times 10^{16}$ molecules/s. The flux of product molecules is $1.1 \times 10^8 s^{-1}$. A background pressure of $6 \times 10^{-6}$ torr is obtained at the vacuum end of the capillary tube, assuming the use of a 50 l/s pump.

Figure 19:
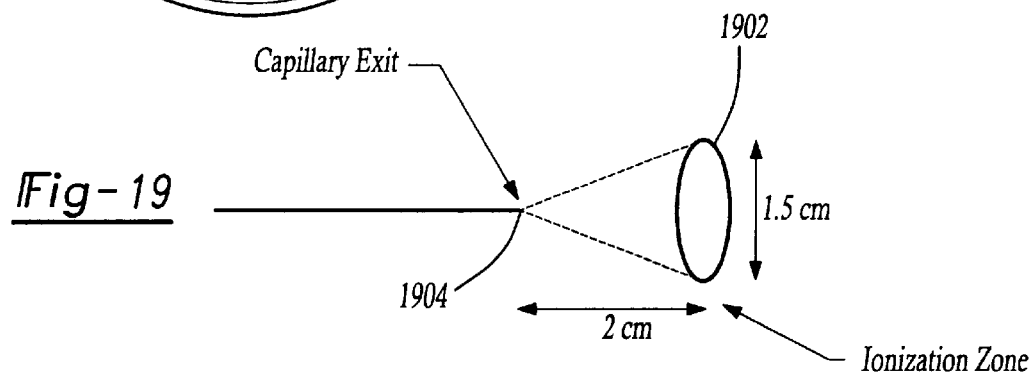
FIG. 19 illustrates the ionization source geometry.

FIG. 19 illustrates the ionization source geometry. The cosine law can be used to describe the molecular density of the molecules exiting the capillary. The integrated form of the differential flux is given by:

$$I(\theta) = I_0(1 - \cos^2 \theta)$$

in which $I_0$ is the total molecule flux through the capillary and $\theta$ is the angle with respect to the capillary axis. Approximately 12% ($1.3 \times 10^{15} s^{-1}$) of the total flux will enter the ionization zone 1902 if the capillary exit 1904 is located 2 cm away.

Assuming a first order reaction, the ionization efficiency is $$dC/dt = C \times \sigma \times N_e \times v_e$$

in which C is the concentration of molecules, $\sigma$ is the molecular electron-ionization cross section, $N_e$ is the electron density, and $v_e$ is the electron speed. From the geometry and operating condition of the ionizer, the product $N_e \times v_e$ is the electron flux which may be estimated. For 2 mA of emission current and a 0.2 cm$^2$ electron beam cross section, $N_e \times v_e = 6.25 \times 10^{16} s^{-1}$. The ionization efficiency coefficient for air is:

$$\eta \equiv \frac{dC}{C dt} = \sigma \times N_e \times v_e = 69 s^{-1}$$

A molecule passing through an electron beam thickness of 0.2 cm requires 4.3 ms. The final electron ionization efficiency is:

$$\frac{\Delta C}{C} = \eta \Delta t = (69s^{-1}) \times (4.3 \times 10^6 s) = 3.0 \times 10^{-4}$$

Therefore, the total number of ions per second is $3.9 \times 10^{11}$, with about 4000 ions of interest per second. Of course, to achieve greater ion production the capillary can be mounted closer to the ionizer and the electron beam can be made thicker.

Although there will be about 4000 ions of interest per second generated in the ionizer, detection of these ions cannot be directly carried out on a conventional quadrupole mass spectrometer. A total of $3.9 \times 10^{11}$ ions are generated in one second therefore requiring a dynamic range on the order of $10^8$. However, the dynamic range for a typical quadrupole mass spectrometer is $10^6$. Accordingly, a quadrupole ion guide is inserted between the ionizer and the mass analyzer to eject unwanted ions selectively.

In a normal quadrupole mass spectrometer, the dynamic range is limited by many factors. Among the most important ones are space charge effects and ion molecule reactions occurring in the mass filter. The insertion of a mass selective ion guide before a QMS allows an additional pumping stage to be inserted between the ionizer and the mass filter and provides a means of reducing the space charge effect through the ejection of the most abundant ions. Conductance limits can be introduced between the vacuum regions in which the ionizer, ion guide, and QMS are located. Therefore, the ionizer can be operated at a high pressure as is typically necessary to achieve the desired sensitivity, while the QMS can be operated at a lower pressure, thus eliminating ion molecule reactions.

In one embodiment, the ion guide comprises a quadrupole assembly with ¾ inch diameter and 8.3 inch long rods. The rod diameter is 3 times larger than that found in a typical RGA since it has to handle 100–1000 more space charges than the last stage QMS. In the common quad rod arrangement, the radius of the inscribed circle is chosen to be 1.1487 times smaller than the radius of the rods necessary to eliminate the forth-harmonic field.

For the ion guide quadrupole, r=0.9525 cm and $r_0$=0.8292 cm. The q-parameter may be expressed as $$q = \frac{4qV}{m\Omega^2 r_0^2} = 1.42 \times 10^{11} \frac{V}{V_{rf}^2 (m/z)}$$

in which V and $\Omega$ are the base-to-peak amplitude and angular frequency of the RF driving signal, respectively, m and z are the mass and charge of the ion, respectively, and $v_{rf}$ is the RF frequency in Hz.

For small values of q, the frequency of the secular or slow motion can be obtained from the following equation $$v_s = \frac{qv_{rf}}{2\sqrt{2}}$$

For an operating frequency of 2.0 MHz and 100 volts of driving amplitude, Table I below lists the important parameters.

TABLE I

| | m/z | q | Vs (kHz) |
|---|---|---|---|
| $CO_2$ | 44 | 0.0807 | 57.05 |
| $O_2$ | 32 | 0.1109 | 78.44 |
| $N_2$ | 28 | 0.1268 | 89.65 |

Figure 20:
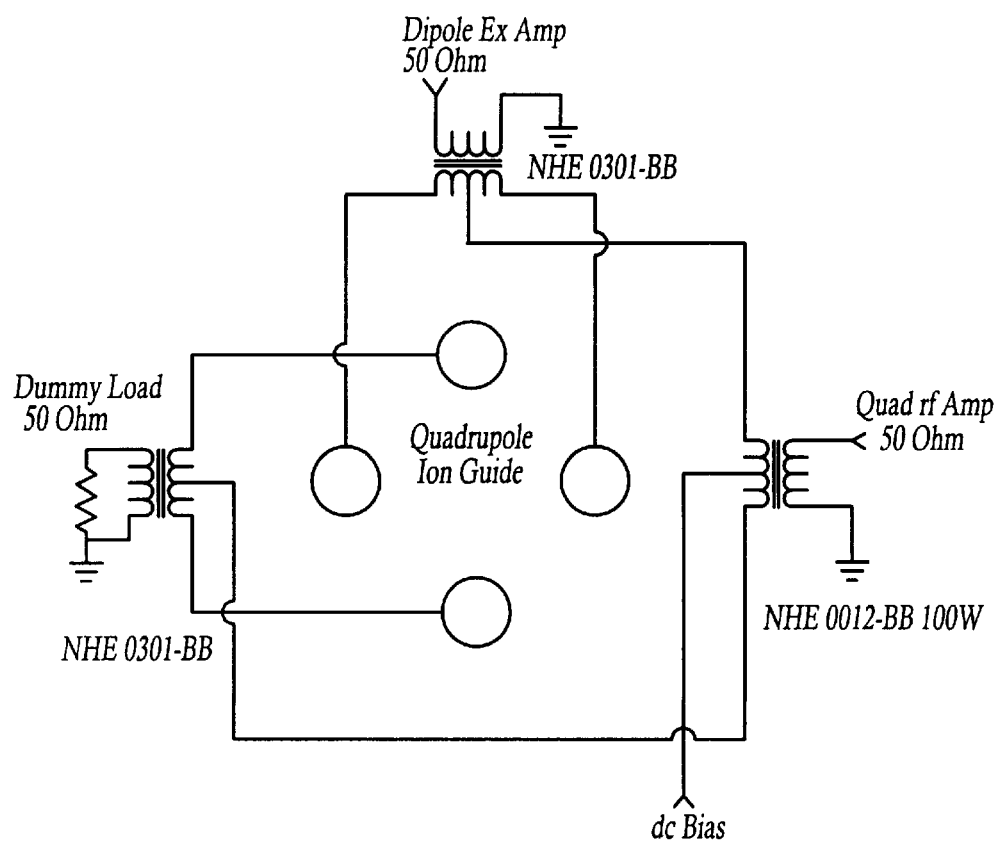
FIG. 20 illustrates a RF transformer-based matching network.

In order to superimpose a bipolar field on a high-amplitude RF quadrupole field, a RF transformer-based matching network is used with the present invention, as illustrated in FIG. 20. The ion secular motion can be described as a forced harmonic oscillator at resonance:

$$\frac{d^2 x}{dt^2} + (2\pi v_s)^2 x = \frac{z}{m} E_0 \cos(2\pi v_s t)$$

in which x is the displacement along the bipolar field applied, $E_0$ is the magnitude of the field, and z and m are charge and mass of the ion, respectively. The solution of the equation with zero initial displacement and zero initial speed is $$x(t) = \frac{zE_0 t}{4\pi m v_s} \cos(2\pi v_s t)$$

It is clear that the profile of x increases linearly with time. In order to estimate the rate of increase, the relation between the applied voltage and the parameter $E_0$ must be established. Although it is possible to obtain an analytical expansion series for the dipole field in an infinite long quadrupole arrangement, it is time consuming and the final parameter evaluation still requires numerical computation from the resultant series. The SIMION program, utilizing a pure numerical simulation, can be used to solve the Laplace equation (D. A. Dahl, *SIMION 3D*, 6.0, Idaho National Engineering Laboratory, 1995). The result is $$E_0 = \frac{0.8018 V_{pp}}{2r_0}$$

in which $V_{pp}$ is the peak-to-peak voltage applied to the facing quadrupole rods.

The bipolar excitation signal contains at least three frequencies as listed in Table I above. It can be synthesized by use of an inverse Fourier transform method. Hardware generation of the signal is provided by an arbitrary waveform generator. The performance for selectively ejecting ions may be theoretically tested with the aid of the SIMION simulation program.

Therefore a fast scanning mass spectrometric instrument in accordance with one embodiment of the invention is capable of sampling at a volume rate of approximately 1 ml/second at one atmosphere pressure. This embodiment can detect small molecules (i.e., up to 250 amu) at a level of 10 ppb per second, thus providing a mass spectrometer that can be used to rapidly screen large arrays of samples.

Figure 21:
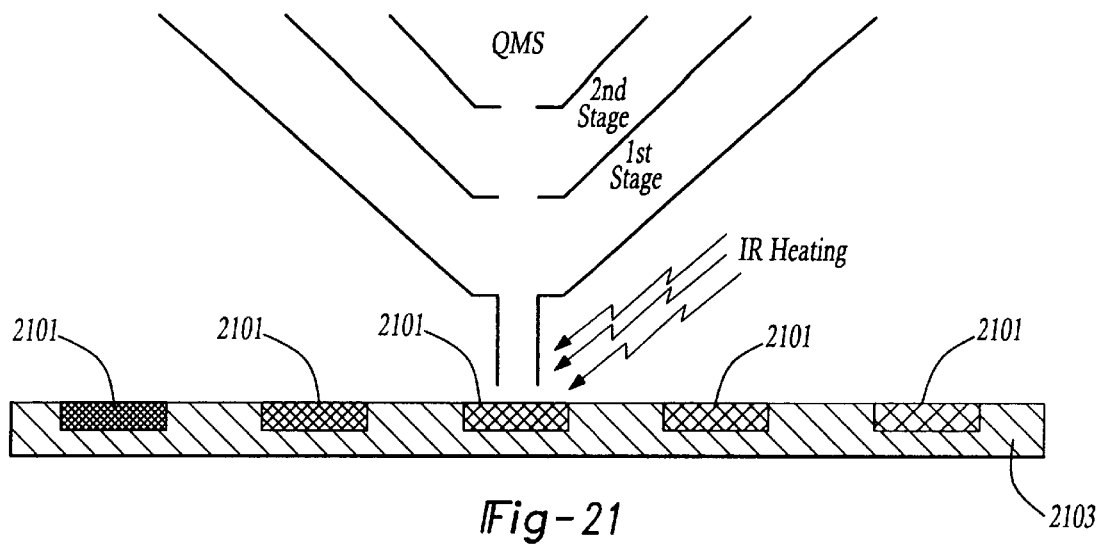
FIG. 21 illustrates an example of a supersonic molecular beam sampling system according to the invention.

Other Scanning Mass Spectrometer Embodiments
Supersonic Molecular Beam Mass Spectrometer Sampling System In this embodiment, a supersonic molecular beam sampling system (SMBSS) depicted in FIG. 21 uses a three staged differentially pumped mass spectrometer system for scanning an array of materials 2101 on a substrate 2103. The supersonic molecular beam sampling system can be applied to a library made by a variety of techniques including, for example, spin coating, vacuum deposition (e.g., e-beam, sputtering, laser ablation, etc.), and various liquid dispensing techniques (e.g., capillary). An example of a suitable substrate 2103 is one made of $SiO_2$ (e.g., oxidized Si wafer). Preferably substrate 2103 is clamped in a susceptor (not shown). In one embodiment, oxidation-reduction of a library is performed in situ. The library elements can be heated simultaneously or sequentially, using IR radiation or resistive heaters patterned on the back of the substrate. The substrate can, for example, contain insertable plugs of supported compounds.

In one embodiment the library has individual elements measuring 1 mm×1 mm with a c/c spacing of 2 mm. Thus on a 3¼ inch by 3¼ inch substrate, a library of 1600 compounds can be formed (i.e., a 40×40 array). Alternatively, a library of 2 mm×2 mm compounds with a c/c spacing of 4 mm gives a library of 20×20 or 400 different compounds. Alternatively, a library of 0.1 mm×0.1 mm elements with a c/c spacing of 0.2 mm gives a library of 400×400 or 160,000 different compounds.

In a particular example of this three stage differentially pumped system, the substrate is approximately 4½ inches× 4½ inches and is comprised of a chemically inert thermal insulator material. Into the substrate approximately 4 mm diameter discs of silicon dioxide or alumina pellets are pressed, each disc containing an individual library element.

In total, the substrate contains 625 compounds. The sampled gas is between about 1 and 5 atm off the library and enters the first stage through a 100 micron aperture. This gives rise to an entrance flux of approximately $2.6\times10^{19}$ molecules per second. The first stage pressure is $1.1\times10^{-3}$ torr using a 1000 l/s turbo molecular pump (TMP). The first stage skimmer has a larger aperture of 200 microns giving rise to a flux through the skimmer $1.2\times10^{14}$ molecules per second. The 200 micron skimmer separates the first stage region (at $1.1\times10^{-3}$ torr) from the second stage which is maintained at a pressure of $1.9\times10^{-8}$ torr by a 200 l/s TMP. The final stage skimmer has a 400 micron aperture extracting approximately $9.2\times10^{9}$ molecules per second in a molecular beam into the final stage maintained at approximately $10^{-3}$ torr (with a diffuse scattered pressure of approximately $8\times10^{-13}$ torr) using a 200 l/s TMP. The effective beam pressure (flux) at the detector is estimated to be approximately $10^{-3}$ torr ($4.1\times10^{16}$ molecules/cm$^2$-s) which provides ample signal for reliable detection.

Single Stage Differentially Pumped Mass Spectrometer

Figure 22:
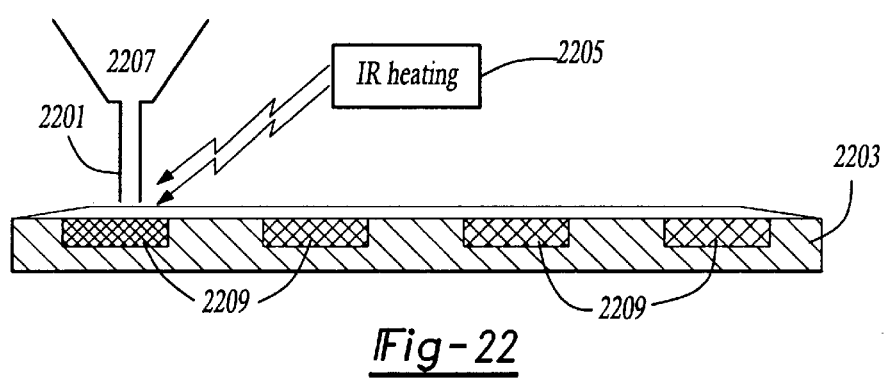
FIG. 22 schematically illustrates a single stage differentially pumped mass spectrometer system with a capillary feed for drawing gas products from a substrate.

FIG. 22 schematically illustrates a single stage differentially pumped mass spectrometer system with a capillary feed 2201 for drawing gas products from a substrate 2203. This system can be applied to a static QMS and rotatable or translatable library. A heat source 2205 is located either above or below the substrate.

Although numerous variations of this implementation exist, in the basic configuration illustrated in FIG. 22, sampling occurs from a circular disc library. A small capillary 2201 with an aperture area of approximately $1.96\times10^{-7}$ cm$^2$ connects the quadrupole mass spectrometer chamber 2207 to the high pressure region (e.g., reactor pressure of $10^3$ torr). The pressure within the mass spectrometer chamber is approximately $7.2\times10^{-6}$ torr which can be achieved using a 270 liter per second turbo molecular pump. Various lengths of capillary or orifice tapers can be used. In the schematic set forth in FIG. 22, if the inlet flow rate is 0.1 liters per second and the pumping speed approximately 1 liter per second, then the steady state reactor pressure is 100 torr and the resonance time is 5 seconds, assuming a reactor volume of 5 liters.

Given a circular sample stage with a 3 inch substrate and 6.35 mm diameter sample discs 2209, 16 different library elements can be used.

Mass Spectrometer with a Simplified Flow System

Figure 23:
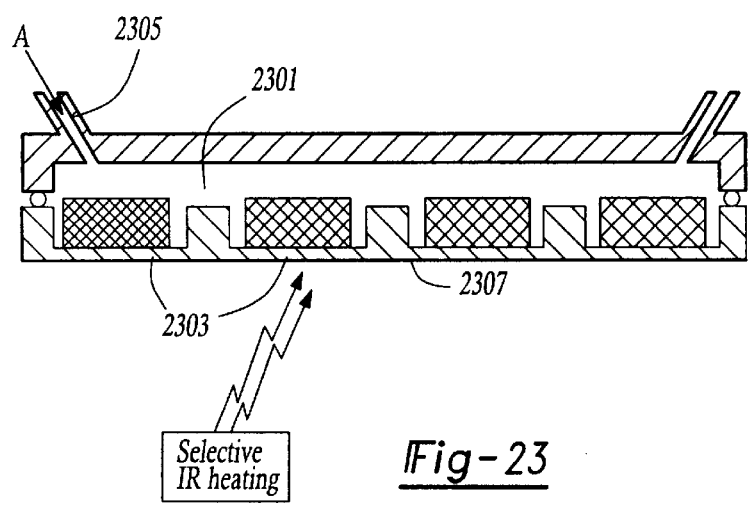
FIG. 23 illustrates an example of a differentially pumped mass spectrometer with a simplified flow system.

A rapid screening method that involves a relatively simple flow system and requires only a scanned IR source is depicted schematically in FIG. 23. As shown, a small volume 2301 is created adjacent to the library 2303 and filled with reactant gas A through an inlet port 2305. Selective IR heating of a thin substrate 2307 can activate a library element of interest, resulting in the creation of products that flow into volume 2301. An outlet 2309 allows the gas to flow out of volume 2301 into a differential mass spectrometer for sampling. If a large number of high molecular weight products exist, a gas chromatograph (not shown) can be implemented prior to the mass spectrometer to separate the products. Maintaining a small volume above the library improves the sensitivity of the mass spectrometric detection. A high surface area support can be used in each library element. To reduce parasitic reactions at other sites, the library can be maintained at a low temperature, wherein only the active element is heated.

A similar arrangement can be configured for a flow-through geometry whereby the inlet is placed on the opposite side of the library as the outlet and the substrate is porous to allow gas passage through each member (not shown).

Heating of the substrate can also be performed by selectively heating regions of the library. In this case a deconvolution strategy is used to determine the elements in the selected regions producing significant signals.

Library of Materials Embedded in Micro-Porous Silica

In another embodiment using a differentially pumped mass spectrometer system, elements are embedded in micro-porous silica capped by macro-porous silica Differential heating of individual element volumes locally increases the diffusivity of the reactants and products through the membrane. As a result, products are more concentrated in the reactor volume above the membrane being sampled by the mass spectrometer.

In this system gas can flow through all of the library elements simultaneously, driven by a pressure gradient wherein the pressure at the bottom is greater than the pressure at the top. Detection is performed from the top (i.e., back of the substrate) in the lower pressure environment. The heat source is applied sequentially to each element. Since the high pressure zone is in contact with the compounds, the compound sees the working pressure of the chamber system. If the pressure behind the plug is greater than 1000 torr, $P_0$ is adjusted to be approximately $10^{-3}$ torr, for example, using a roughing pump and the membrane porosity. A mass spectrometer with an orifice of 1 micron gives rise to a flux of $3.2\times10^{17}$ molecules/cm$^2$-s. The leak rate is $2.5\times10^{15}$ molecules per second and $P_1$ is $7.8\times10^{-7}$ torr, assuming a 100 l/s turbo molecular pump.

Individual Flow-Through Library Sampling

The individual flow-through libraries system is similar to the embedded catalyst impregnated in micro-porous silica capped system described above, except that this embodiment employs individual flow-though paths through each library element so that the introduction of reactants can be performed sequentially. This system provides a distinct advantage in that it enables products to be more concentrated in the product outlet stream.

In an individual flow through library implementation, typically fewer library elements are employed (for example, an 8×12 array), thus providing extremely high concentrations of products in the outlet stream. The pressure drop through the porous support dictates the flow into the vacuum side. For 1 cc/s at 1000 torr, a flux of $3.5 \times 10^{19}$ molecules per second is obtained. The vacuum pressure is 0.2 torr using a 10 micron diameter orifice into the quadrupole mass spectrometer. A turbo molecular pumping speed of 100 l/s gives rise to a pressure in the mass spectrometer of $1.7 \times 10^{-8}$ torr.

Delivery Through A Gas Manifold

Figure 24:
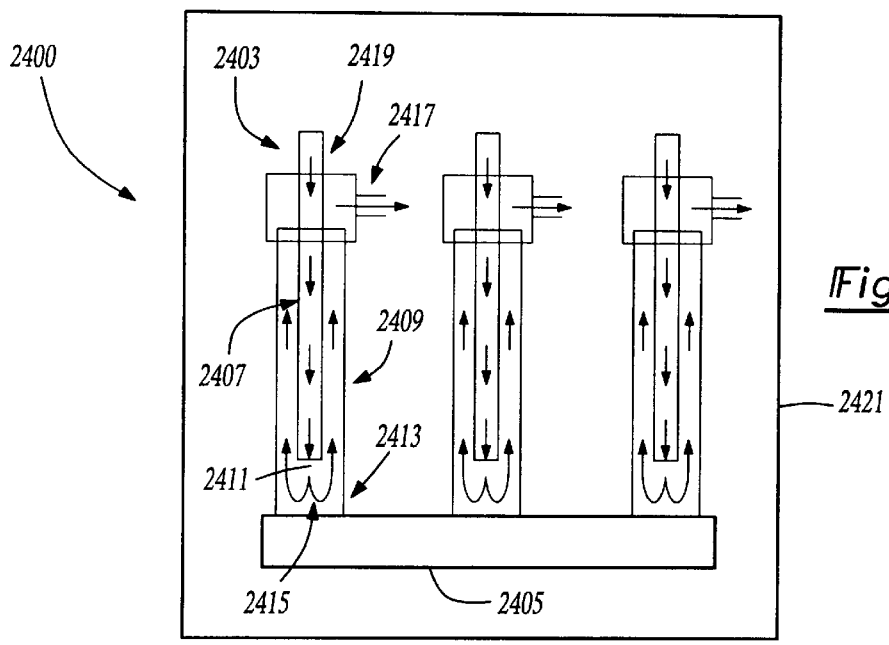
FIG. 24 illustrates an embodiment of the present invention wherein an array of sampling probes is employed to screen materials at predefined regions of the substrate.
Figure 25:
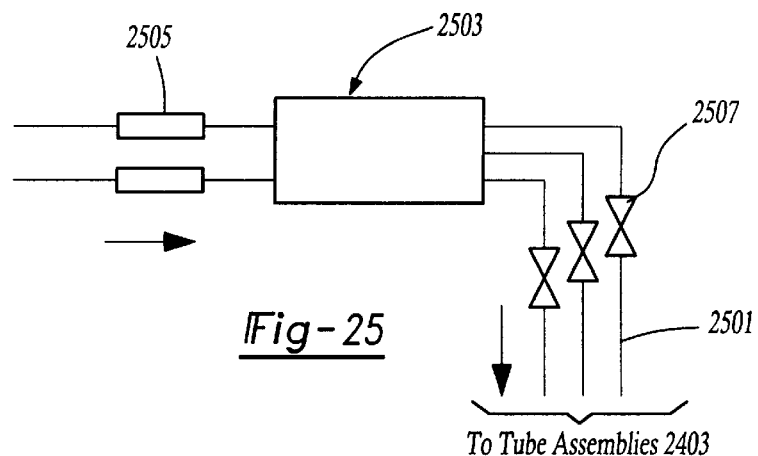
FIG. 25 illustrates the gas manifold system of the embodiment shown in FIG. 24.
Figure 26:
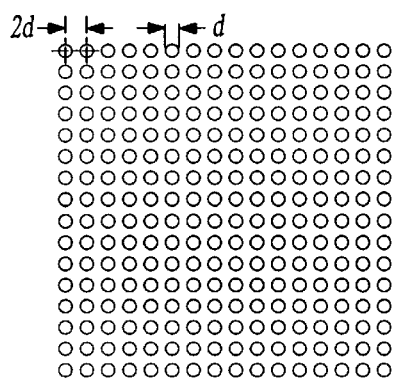
FIG. 26 illustrates a 16×16 matrix for use with a combinatorial catalyst library.
Figure 27:
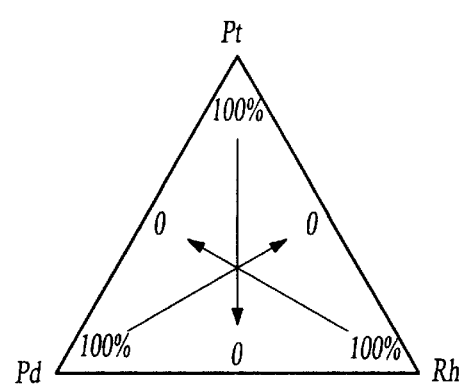
FIG. 27 illustrates the Pt—Pd—Rh ternary phase diagram.

FIGS. 24 and 25 illustrate an alternative system and method for spatially drawing components from predefined regions on a substrate into the ionization chamber of the mass spectrometer. This system and method generally provides an array of sampling probes, rather than a single probe that is scanned across the substrate. Among other applications, the system and method of FIGS. 27 and 28 may be used for chemical reaction studies, such as heterogenous catalysis or corrosion studies, and/or material annealing and treatment (e.g., reduction, oxidation, diffusion, thermal growth of oxides, nitrides and other films).

As shown in FIG. 24, a system 2400 includes an array of spaced gas exposure tube assemblies 2403 for delivering and drawing gas(es) from predefined regions on a substrate 2405. The number and spacing of gas exposure tube assemblies 2403 will, of course, depend on the number and spacing of the predefined regions on substrate 2405. Each tube assembly 2403 includes inner and outer concentric tubes 2407 and 2409, respectively, for delivering and removing gas(es) from substrate 2405. Typically, reactant gas is delivered through inner tube 2407, which has an outlet 2411 spaced inward from the distal end 2413 of outer tube 2409. The gas flows vertically or horizontally through inner tube 2407, where it interacts with a small region 2415 of the surface of substrate 2405. The products of the reaction are drawn back through inner tube 2407 and are exhausted through the annular cavity and into the ionization chamber of the spectrometer in a manner similar to that described above in reference to FIGS. 8–10. Alternatively, exhaust lines 2417 may also include two-way valves (not shown) so that each line can be sampled to facilitate rapid, sequential screening of the reaction regions.

As shown in FIG. 24, tube assemblies 2403 preferably include a proximal fitting 2419 that fluidly couples an exhaust line 2417 with the annular cavity. As shown in FIG. 25, inner tubes 2407 are each coupled, via supply lines 2501, to one or more gas manifolds 2503. Preferably, gas manifolds 2503 are common to more than one inner tube 2407. A mixture of gases controlled by mass flow controllers 2505 are fed into manifold(s) 2503. The different manifolds may be set up with different concentrations of a gas mixture or completely different gas mixtures. Supply lines 2501 preferably each have independently controlled valves 2503 for varying the gas mixture applied to each region 2415 of substrate 2405, and/or for varying the exposure time of the gases within manifold(s) 2503 to each predefined region 2415. Varying the exposure time may impact reaction time at region 2415.

In use, one or more reactant gases are delivered in varying or equal concentrations to one or more of the gas manifold(s) 2503. Valves 2507 are opened and closed to allow the gas mixture within manifold(s) 2503 to pass from supply lines 2501 through inner tubes 2407 to the region 2415 over substrate 2405. The exposure time of the materials at each region 2415 to the gas(es) can be varied by varying the amount of time each valve 2507 is opened, or by varying the flow rate through each valve 2507. As shown in FIG. 24, each exposure is preferably localized by contacting the substrate 2405 with distal end 2413 of outer tubes 2409. In addition, tube assemblies 2403 are preferably located within a vessel 2421 that is purged with an inert gas maintained at a slightly higher pressure than the gas within exposed regions 2415. This pressure difference leads to an inward leakage of the inert gas rather than an outward leakage of the reactants. The products of the reaction are then drawn back through inner tubes 2407 to the ionization chamber, while the remaining reactant gases are exhausted through outer tubes 2409.

Preparation of Combinatorial Libraries

The following examples are offered for illustrative purposes, and are not intended to limit the invention in any manner. Those of skill in the art will readily recognize a variety of non-critical parameters that can be changed or modified to yield essentially the same results. Furthermore, although several of the following examples are limited to combinatorial catalyst libraries, the present invention is not so limited. The present invention is equally applicable to combinatorial libraries comprised of, for example, covalent network solids, ionic solids and molecular, inorganic materials, intermetallic materials, metal alloys, ceramic materials, organic materials, organometallic materials, non-biological organic polymers, composite materials (e.g., inorganic composites, organic composites, or combinations thereof), as well as homogeneous or heterogeneous catalysts.

Combinatorial Catalyst Libraries

Combinatorial catalyst libraries were deposited on substrates or wafers comprised of quartz, glass, silicon, sapphire, aluminum oxide, magnesium oxide and lanthanum aluminum oxide. The substrates were chemically modified using organosilane reagents. Silanes, such as $CH_3(CH_2)_nSiCl_3$ where $0 \leq n \leq 17$, were chosen to lend hydrophobic characteristics to the substrate surface. Substrates were sonicated for 15–20 minutes in isopropanol, rinsed with distilled, de-ionized $H_2O$, dried under an $N_2$ gas jet and heated at 120° C. for 20–30 minutes. After cooling, substrates were placed in a 5% v/v solution of silane and $CH_2Cl_2$ for 10 minutes, washed in $CH_2Cl_2$ and methanol, and dried under an $N_2$ gas jet. The entire process was then repeated and the substrates were heated at 120° C. for 20–30 minutes.

Figure 29:
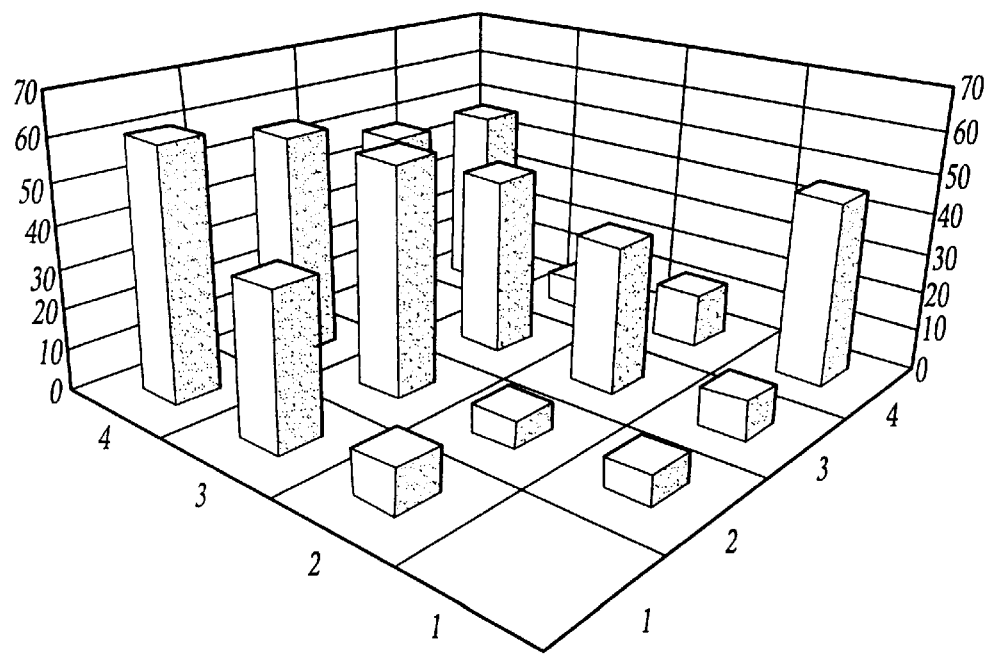
FIG. 29 illustrates the characterization of a ternary Sn—Ru—Pt library having 16 different compositions in which the library elements were tested for activity with respect to the oxidation of carbon monoxide using a scanning mass spectrometer.

After the substrates were chemically modified through silanization, the silanized wafer surface was physically modified by bead blasting with 50 $\mu$m alumina grit. Rectangular matrices were constructed of aluminum for masking purposes. An example 16×16 matrix is illustrated in FIG. 29. Variable matrix element densities masks may be used, where the diameter, d, equals 1, 1.5 or 3 mm, and where the center-to-center spacing between matrix elements equals 2d. Wafers were manually bead blasted for approximately 5 minutes. Profilometry of bead blasted wafers was routinely investigated to ascertain the depth and consistency of the etched wells.

System A: Oxidation of carbon monoxide to carbon dioxide

Catalysts for the oxidation of CO may be prepared in a combinatorial library format as described below. The composition of each library matrix element is given as the percentage of each constituent element.

Example 1

Pt—Pd—Rh

Approximately 0.5 mmol of $H_2PtCl_6$ hydrate, $Pd(NO_3)_2$ solution and $RhCl_3$ were diluted in DDI $H_2O$ resulting in constituent solutions with a concentration of 0.2M. Using a Cavro RSP 9000 automated liquid dispensing system, a ternary phase diagram was constructed. Volumes of each solution were dispensed into a 96-well microtiter plate in ratios such that 100 μl of metal solution was present in 66 wells for the purpose of creating an 11×11×11 triangular matrix. Thus, rows of the triangle were decremented in units of 10%. 50 μl of ethylene glycol was added to each microtiter well to assist in efficiently wetting the substrate surface ensuring film quality. To insure adequate mixing, the microtiter plate was placed on an agitator table for 10 minutes. 0.5–3 μl of each solution was then deposited onto the substrate either in an automated fashion using the Cavro liquid dispensing system or manually using an Eppendorf micropipette. By virtue of the chemical and physical surface modifications described above, solutions at each matrix element were effectively isolated from one another.

Prepared combinatorial libraries were then dried in air at 120° C. for up to 12 hours. After the library was dried, decomposition of the solution precursors was affected by heating between 12–24 hours at 500° to 1000° C. in air, argon or 10% hydrogen in argon. Specific heating times, temperatures and atmospheres were determined by the precursors in question.

After preparation of the library was completed but before catalytic testing was begun, routine characterization techniques were performed to ensure reproducibility. These characterization techniques included but were not limited to x-ray powder diffraction (XRD) for phase identification, optical and electron microscopy for film quality and particle size, and energy dispersive spectroscopy (EDS) for elemental mapping.

Example 2
Pt—Pd—Au

Approximately 0.5 mmol of $H_2PtCl_6$ hydrate, $Pd(NO_3)_2$ solution and $HAuCl_4$ were diluted in DDI $H_2O$ resulting in constituent solutions with a concentration of 0.2M. Solutions were dispensed into a microtiter plate, and subsequently onto a surface modified substrate as described in Example 1 above.

Combinatorial libraries of the Pt—Pd—Au phase space were then dried and calcined as described in Example 1 above.

Example 3
Pt—Pd—Ag

Approximately 0.5 mmol of $Pt(NH_3)_4(NO_3)_2$, $Pd(NO_3)_2$ solution and $AgNO_3$ were diluted in DDI $H_2O$ resulting in constituent solutions with a concentration of 0.2M. Solutions were dispensed into a microtiter plate, and subsequently onto a surface modified substrate as described in Example 1 above.

Combinatorial libraries of the Pt—Pd—Ag phase space were then dried and calcined as described in Example 1 above.

System B: Oxidative dehydrogenation of ethane to ethylene

Combinatorial libraries of catalytic materials for the purpose of the oxidative dehydrogenation of ethane to ethylene may be prepared according to the methods described below. Substrates were prepared in the same fashion as that described above.

Example 4
Mo—V—Nb—O

Approximately 5 mmol $NbCl_5$ was slowly hydrolyzed in DDI $H_2O$. The solution was neutralized with $NH_4OH$ resulting in a white, gelatinous solid. The solid was filtered and washed repetitively with DDI $H_2O$. After drying, the white solid was redissolved in a hot oxalic acid solution resulting in a 0.3M solution of Nb oxalate. The niobium solution was diluted to 0.25M. Approximately 15 mmol $NH_4VO_3$ was dissolved with stirring in DDI $H_2O$ at 75° C. resulting in a 0.25M solution. 2.5 mmol $(NH_4)_6Mo_7O_{24}$:$4H_2O$ was dissolved in a minimum of DDI $H_2O$ with stirring at 75° C. The resulting solution was diluted to 0.25M.

Volumes of each solution were dispensed into a 96-well microtiter plate in ratios such that 100 μl of metal solution was present in 66 wells for the purpose of creating an 11×11×11 triangular matrix as described above. Rows of the triangle were decremented in units of 10% resulting in 100% Mo—O, 100% V—O and 100% Nb—O species at the three corners of the triangle. Ethylene glycol was also added to each microtiter well to assist in efficiently wetting the substrate surface ensuring film quality. The microtiter plate was placed on an agitator table for 10 minutes to aid in mixing. 0.5–3 μl of each solution was then deposited onto the substrate either in an automated fashion using the Cavro liquid dispensing system or manually using an Eppendorf micropipette.

As prepared combinatorial libraries were then dried in air at 120° C. for up to 16 hours or until complete drying occurred. After the library was dried, decomposition of the solution precursors was affected by heating for less than 4 hours at no more than 400° C. in air. Libraries were characterized as described above before catalytic testing was begun.

Example 5
Mo—V—Nb—O

Alternate methods for the preparation of combinatorial libraries for the oxidative dehydrogenation of ethane were also investigated.

Niobium and molybdenum solutions were prepared as described in Example 4 above. Ammonium vanadate was dissolved in 50:50 DDI $H_2O$:HCl. The resulting vanadium solution was diluted to 0.25M. Ethylene glycol was added to aid in wetting. Solutions were then deposited as described above, first into a microtiter plate and subsequently onto a substrate material. Libraries were dried and calcined as described above.

Example 6
Mo—V—Nb—O

Approximately 2 mmol $MoOCl_4$ was dissolved in 2,3-pentanedione at 0° C. under argon. The resulting brown viscous solution comprised of niobium (V) ethoxide and vanadium (V) tris-isopropoxide oxide was diluted to 0.125M in anhydrous 2-methoxyethanol. Dry ethylene glycol was added to aid wetting. Solutions were deposited into microtiter plates and subsequently onto substrate materials as described above. After deposition, libraries were dried for at least 24 hours in an atmosphere of 2-methoxyethanol. After gelation, libraries were gradually dehydrated through a heating cycle consisting of slow (1°/min) ramping followed by 16 hours at 120° C. and no more than 4 hours at 400° C.

Example 7
Mo—V—Nb—O

Approximately 5 mmol of $MoCl_5$, $VCl_4$ and $NbCl_5$ were dissolved with stirring in a minimum of 2-methoxyethanol at 0° C. under flowing argon. The resulting solutions were purged with argon to purge out as much HCl as possible, after which the solutions were diluted to 0.125M. Solutions were deposited into a 96-well microtiter plate and subsequently onto surface modified substrate materials as described above. Ethylene glycol as added as a wetting agent and DMF was added to aid in crack-free drying. The libraries were allowed to dry under an atmosphere of 2-methoxyethanol for at least 24 hours or until gelation occurred. After gelation the libraries were gradually dehydrated at 120° C. for no more than 16 hours and calcined at no more than 400° C. for 2–4 hours.

Example 8
Sn—Ru—Pt Library Tested for Activity (Oxidation of Carbon Monoxide)

This example illustrates the use of a 4×4 spatially addressable array to test for a specific property, namely the oxidation of carbon monoxide.

In this example, an array of 16 indium tin oxide (ITO) electrodes was fabricated on a glass substrate in order to allow the electrochemical deposition of metals from solution. Three different combinatorial approaches to the fabrication of the electrochemically deposited array were explored on a single substrate, illustrating the versatility of the technique. By varying the composition of the electroplating solutions, applying varying potentials to the electrodes, and using metals that have differing reduction potentials, complicated ternary metal compositions can be achieved in a simple 4×4 array. Although not explored in this example, single element serial deposition steps, variations in the time and the amount of current passed, and increasing the number of metal ions to be deposited from solution (more than three) are obvious variants to develop more intricate libraries.

For this example, the ternary Sn—Ru—Pt library was prepared using solutions of 0.1M $H_2PtCl_6$, 0.1M $RuCl_3$ and 0.1M $SnCl_2$ in 0.5M $H_2SO_4$. In a deposition chamber the 4×4 ITO array, a silver/silver chloride (Ag/AgCl) reference electrode, and a platinum mesh counter electrode were set up. After the addition of the appropriate amount of a particular electroplating solution, a given electrode was addressed by connecting it to a potentiostat and applying a predetermined series of voltage pulses using potential square wave voltammetry. In this example each of the electrodes was first subjected to a 1 second voltage pulse of 0 volts versus the reference electrode followed by a 1 second pulse at a predetermined potential between –0.3 volts and –1 volt before being returned to 0 volts. A total of 30 of these cycles were applied to each electrode.

Figure 28:
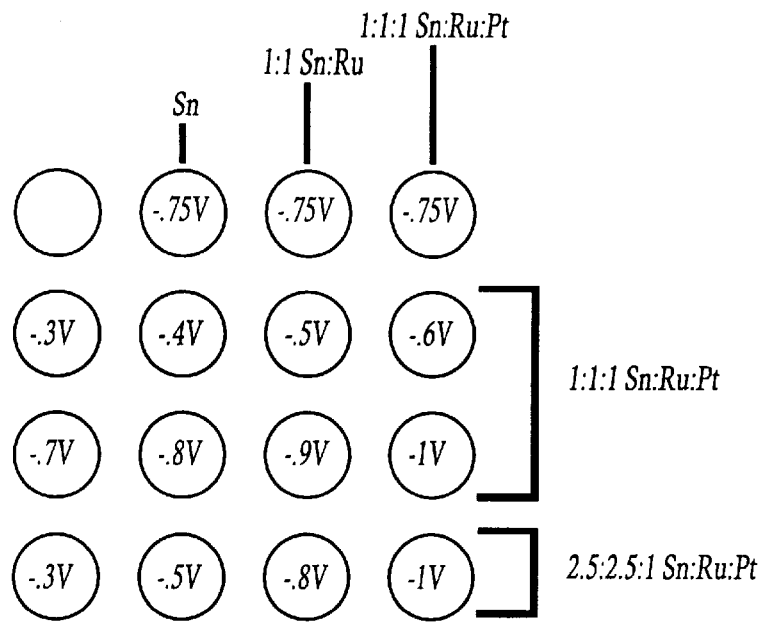
FIG. 28 illustrates the different solution compositions and potentials applied to an array to form a combinatorial Sn—Ru—Pt library.

FIG. 28 illustrates the conditions under which the ternary Sn—Ru—Pt library described in this example was prepared. Electrode 1,1 (column, row) was intentionally left blank in order to later determine the indium and tin compositions of the underlying ITO electrodes. Row 1 was prepared at a constant potential of –0.75 volts while the solution content was varied from pure Sn (electrode 1,2) to 1:1 Sn:Ru (electrode 1,3) to 1:1:1 Sn:Ru:Pt (electrode 1,4). Rows 2 and 3 were prepared by keeping the solution composition constant (1:1:1 Sn:Ru:Pt) while varying the potential between –0.3 volts and –1 volts. Row 4 was prepared by varying the solution composition in favor of the less easily reduced metals (Sn and Ru) while sequentially varying the potential between –0.3 volts and –1 volt.

Although four different solutions are required to prepare the complete Sn—Ru—Pt library, removal and replacement of portions of the solutions starting with pure 0.1M $SnCl_2$ and ending up with a 2.5:2.5:1 Sn:Ru:Pt solution is easily accomplished in situ and eliminates the need for rinsing steps. Starting with the pure Sn solution, the electrochemical deposition of Sn metal is accomplished on electrode 1,2. Removing exactly half of this solution and replacing it with an equivalent amount of the 0.1M $RuCl_3$ solution gives a 1:1 Sn:Ru solution used for the deposition of a Sn/Ru composition on electrode 1,3. Removing exactly one third of this solution and replacing it with an equivalent amount of the 0.1M $H_2PtCl_6$ solution gives a 1:1:1 Sn:Ru:Pt solution used for the depositions of Sn/Ru/Pt compositions on electrodes 1,4 to 3,4. Removing exactly one half of this solution and replacing it with an equivalent amount of the 1:1 Sn:Ru solution gives a 2.5:2.5:1 Sn:Ru:Pt solution used for the deposition of Sn/Ru/Pt compositions on electrodes 4,1 to 4,4. According to this procedure, at no time does the array need to be removed from the bath in order to complete the ternary Sn—Ru—Pt library.

The results of the above-described depositions showing the percentages of Sn, Ru and Pt (corrected for the Sn content of the underlying ITO electrodes and normalized to 100%) plated out on each electrode are summarized in Table II.

TABLE II

| Electrode | % Sn | % Ru | % Pt |
| --- | --- | --- | --- |
| 1,1 | 0 | 0 | 0 |
| 1,2 | 100 | 0 | 0 |
| 1,3 | 77.3 | 22.7 | 0 |
| 1,4 | 23.1 | 13.5 | 63.4 |
| 2,1 | 12.3 | 24.2 | 63.5 |
| 2,2 | 17.7 | 16.1 | 66.2 |
| 2,3 | 17.9 | 14.9 | 67.2 |
| 2,4 | 14.9 | 13.3 | 71.8 |
| 3,1 | 8.3 | 14.4 | 77.3 |
| 3,2 | 8.5 | 9.7 | 81.8 |
| 3,3 | 13.5 | 13.1 | 73.4 |
| 3,4 | 10.8 | 13.8 | 75.4 |
| 4,1 | 17.3 | 28.3 | 54.4 |
| 4,2 | 20.6 | 28.2 | 51.2 |
| 4,3 | 22.2 | 28.6 | 49.2 |
| 4,4 | 22.8 | 26.2 | 51.0 |

From this table some obvious and expected trends are observed in the electrochemical deposition process. As expected, electrode 1,2 contains only Sn; electrode 1,3 contains a mixture of Sn and Ru; and electrode 1,4 contains a mixture of Sn, Ru and Pt. In general, since the Pt solution is easiest to reduce, more negative potentials tend to plate out more Pt. Comparison of the percent of Pt found in electrodes 2,1 through 3,2, for example, shows this trend nicely. This phenomenon can be counteracted by reducing the concentration of Pt in solution as was done in the case of electrodes 4,1 through 4,4.

When compared to electrodes 1,4 through 3,4 which were prepared from the 1:1:1 Sn:Ru:Pt electroplating solution, the 1,4 to 4,4 electrodes show a dramatic decrease in the percentage of Pt in the final deposit corresponding to the decrease in the ratio of Pt in the 2.5:2.5:1 Sn:Ru:Pt electroplating solution. Similar trends to those described above exist for the Sn and Ru species in this example.

Each electrode in the library described above was tested for activity with respect to the oxidation of carbon monoxide (CO) using a scanning mass spectrometer. Using a vacuum-compatible epoxy, two opposite edges of the substrate were affixed to segments of silicon cleaved from a 3 inch diameter silicon wafer. Use of the silicon segments, which supported the substrate in the scanning mass spectrometer holder, permitted the substrate to be heated from the backside using a $CO_2$ laser. After the epoxy hardened, the substrate and silicon segments were clamped into a sample holder and placed in the scanning mass spectrometer for testing.

Inside the scanning mass spectrometer, each electrode was tested individually. With the pressure inside the reaction chamber of the scanning mass spectrometer at approximately 1 atmosphere, each electrode was heated to 400° C. under a flow of carbon monoxide (0.1 sccm), oxygen (0.4 sccm), and argon (2.0 sccm). After the temperature equilibrated to a steady value, the concentration of carbon dioxide (CO) in the exhaust gas was measured over approximately 30 seconds. The results are shown in FIG. 29 where the $CO_2$ production is plotted as a function of the individual electrodes. It is well known that Pt is an excellent catalyst for the oxidation of CO. Not surprisingly, therefore, those electrodes with a high percentage of Pt (like electrode 3,2) showed activity for the oxidation of CO, while those electrodes with little or no Pt content (like electrodes 1,2 or 1,3) showed little or no activity for this process. Depending primarily on their Pt content, the other electrodes in the array showed varying activity towards the oxidation of CO.

As will be understood by those familiar with the art, the present invention may be embodied in other specific forms without departing from the spirit or essential characteristics thereof. Accordingly, disclosure of the preferred embodiment of the invention is intended to be illustrative, but not limiting, of the scope of the invention set forth in the following claims.

What is claimed is:

1. A method of screening materials arrayed on a substrate comprising:
   providing a plurality of materials arrayed on the substrate
   reacting each of the materials arrayed on the substrate with one or more gas-phase reactants to form one or more products;
   obtaining gas samples from locations adjacent to the materials following the reacting step; and
   measuring an amount of at least one of the products in each of the gas samples by mass spectrometry.

2. The method of claim 1, wherein measuring further comprises determining relative concentrations of at least one of the products and at least one of the gas-phase reactants in each of the gas samples by mass spectrometry.

3. The method of claim 1, wherein contacting further comprises heating the materials to a temperature sufficient to promote conversion of the gas-phase reactants to the products.

4. The method of claim 3, wherein contacting further comprises heating the materials to a temperature insufficient to cause the materials to undergo thermal desorption.

5. The method of claim 1, wherein obtaining further comprises:
   positioning a gas inlet of a sampling probe adjacent one of the materials arrayed on the substrate; and
   drawing one of the gas samples through the gas inlet of the sampling probe.

6. The method of claim 5, wherein positioning and drawing are carried out for each of the materials arrayed on the substrate by moving the gas inlet of the sampling probe across the substrate.

7. The method of claim 5, further comprising heating the materials to a temperature sufficient to promote conversion of the gas-phase reactants to the products prior to drawing one of the gas samples.

8. The method of claim 7, wherein contacting further comprises heating the materials to a temperature insufficient to cause the materials to undergo thermal desorption.

9. The method of claim 7, wherein contacting further comprises heating one of the materials to a temperature insufficient to cause the materials to undergo thermal desorption.

10. The method of claim 5, further comprising heating one of the materials to a temperature sufficient to promote conversion of the gas-phase reactants to the products prior to drawing one of the gas samples.

11. The method of claim 1, wherein obtaining further comprises:
    positioning a plurality of sampling probes adjacent to a portion of the materials arrayed on the substrate, the plurality of sampling probes having gas inlets, each of the gas inlets located adjacent different materials; and
    drawing gas samples through the gas inlets of the plurality of sampling probes.

12. The method of claim 11, wherein each of the gas samples are sequentially drawn through the plurality of sampling probes.

13. The method of claim 1, wherein the substrate is micro-porous silica and the materials are capped by macro-porous silica membrane.

14. The method of claim 13, further comprising selectively heating the materials prior to obtaining gas samples, wherein heating increases diffusion rate of the gas samples through the macro-porous silica membrane.

15. The method of claim 1, wherein measuring occurs at a rate of at least one gas sample per second.

16. The method of claim 15, wherein measuring occurs at a rate of at least ten gas samples per second.

17. The method of claim 15, wherein measuring occurs at a rate of at least one hundred gas samples per second.

18. The method of claim 1, further comprising:
    ionizing the gas samples; and
    filtering the gas samples following the ionizing step with a quadrupole ion guide prior to measuring.

19. The method of claim 1, wherein each of the materials arrayed on the substrate are contacted with two gas-phase reactants.

20. The method of claim 1, wherein each of the materials arrayed on the substrate are contacted with three gas-phase reactants.

21. The method of claim 1, wherein two products in each of the gas samples are measured by mass spectrometry.

22. The method of claim 1, wherein three products in each of the gas samples are measured by mass spectrometry.

23. The method of claim 1, wherein the total time for completing contacting, obtaining and measuring is on average less than about one hundred seconds for each of the materials.

24. The method of claim 23, wherein the total time for completing contacting, obtaining and measuring is on average less than about ten seconds for each of the materials.

25. The method of claim 24, wherein the total time for completing contacting, obtaining and measuring is on average less than about one second for each of the materials.

26. The method of claim 25, wherein the total time for completing contacting, obtaining and measuring is on average less than about 0.1 second for each of the materials.

27. The method of claim 26, wherein the total time for completing contacting, obtaining and measuring is on average less about 0.01 second for each of the materials.

28. A system for screening materials arrayed on a substrate by detecting at least one of reaction products in gas samples obtained from locations adjacent to the materials, the system comprising:
    a substrate;
    a plurality of materials arrayed on the substrate;
    one or more sources of gas-phase reactants for reacting each of the materials arrayed on the substrate with one or more gas-phase reactants to form one or more products;

a conduit system for obtaining gas samples from locations proximate to the materials arrayed on the substrate, wherein the conduit system comprises at least one sampling probe having a gas inlet located proximate to at least one of the materials;

a reaction chamber enclosing at least the gas inlet portion of the sampling probe and the substrate, the reaction chamber in fluid communication with the sources of the gas-phase reactants;

an ionization chamber associated with a mass spectrometer system, wherein the gas samples pass through the conduit system into the ionization chamber where the gas samples are ionized;

a filter in fluid communication with the ionization chamber for selectively blocking passage of selected ions from ionized gas samples; and a collector coupled to the filter, wherein the collector outputs a signal responsive to a concentration of ions passing through the filter.

29. The system of claim 28, further comprising a translation stage attached to the substrate for moving the substrate relative to the sampling probe in order to obtain gas samples adjacent each of the materials.

30. The system of claim 28, wherein the conduit system comprises a plurality of sampling probes, the plurality of sampling probes having gas inlets associated with different materials arrayed on the substrate.

31. The system of claim 28, wherein the conduit system provides fluid communication between the sources of the gas-phase reactants and reaction chamber, and the conduit system is adapted to selectively contact the materials with the gas-phase reactants.

32. The system of claim 31, further comprising a heating source coupled to the substrate, the heating source configured to selectively heat the materials arrayed on the substrate.

33. The system of claim 31, wherein the sampling probe has a gas outlet adjacent the gas inlet for introducing the gas-phase reactant near one of the materials arrayed on the substrate.

34. The system of claim 28, wherein the mass spectrometer is a supersonic molecular beam mass spectrometer.

35. The system of claim 28, further comprising a heating source coupled to the substrate, the heating source configured to selectively heat the materials arrayed on the substrate.

* * * * *